US009661857B2

(12) United States Patent
Yamashita

(10) Patent No.: US 9,661,857 B2
(45) Date of Patent: May 30, 2017

(54) COMPOSITIONS FOR CONTROLLING PLANT PARASITIC NEMATODES

(71) Applicant: Thomas T. Yamashita, Turlock, CA (US)

(72) Inventor: Thomas T. Yamashita, Turlock, CA (US)

( * ) Notice: Subject to any disclaimer, the term of this patent is extended or adjusted under 35 U.S.C. 154(b) by 0 days.

(21) Appl. No.: 14/473,470

(22) Filed: Aug. 29, 2014

(65) Prior Publication Data
US 2015/0125435 A1 May 7, 2015

Related U.S. Application Data

(60) Provisional application No. 61/899,023, filed on Nov. 1, 2013.

(51) Int. Cl.
| | |
|---|---|
| *A01N 27/00* | (2006.01) |
| *A01N 63/04* | (2006.01) |
| *A01N 37/10* | (2006.01) |
| *A01N 41/04* | (2006.01) |
| *A01N 31/08* | (2006.01) |
| *A01N 31/16* | (2006.01) |
| *A01N 37/02* | (2006.01) |
| *A01N 37/38* | (2006.01) |
| *A01N 37/40* | (2006.01) |
| *A01N 43/08* | (2006.01) |
| *A01N 43/12* | (2006.01) |
| *A01N 43/30* | (2006.01) |
| *A01N 43/90* | (2006.01) |
| *A01N 63/00* | (2006.01) |

(52) U.S. Cl.
CPC ............ *A01N 63/04* (2013.01); *A01N 27/00* (2013.01); *A01N 31/08* (2013.01); *A01N 31/16* (2013.01); *A01N 37/02* (2013.01); *A01N 37/10* (2013.01); *A01N 37/38* (2013.01); *A01N 37/40* (2013.01); *A01N 41/04* (2013.01); *A01N 43/08* (2013.01); *A01N 43/12* (2013.01); *A01N 43/30* (2013.01); *A01N 43/90* (2013.01); *A01N 63/00* (2013.01)

(58) Field of Classification Search
None
See application file for complete search history.

(56) References Cited

U.S. PATENT DOCUMENTS

| | | | |
|---|---|---|---|
| 3,034,952 A | 5/1962 | Beames et al. | |
| 5,696,094 A * | 12/1997 | Yamashita | A01N 41/04 424/DIG. 8 |
| 6,210,953 B1 * | 4/2001 | Osman | C07K 14/325 435/252.5 |
| 6,309,440 B1 | 10/2001 | Yamashita | |
| 9,302,948 B2 * | 4/2016 | Yamashita | C05F 11/08 |
| 2002/0045661 A1 | 4/2002 | Omilinsky | |
| 2010/0068299 A1 | 3/2010 | van der Krieken et al. | |
| 2012/0174640 A1 * | 7/2012 | Yamashita | C05D 9/02 71/23 |
| 2013/0029844 A1 * | 1/2013 | Altier | C07K 14/415 504/100 |
| 2013/0312469 A1 * | 11/2013 | Yamashita | C05D 9/02 71/23 |
| 2014/0030369 A1 * | 1/2014 | Yamashita | A01N 37/40 424/780 |
| 2015/0075239 A1 * | 3/2015 | Yamashita | C05D 9/02 71/23 |
| 2015/0239788 A1 * | 8/2015 | Yamashita | C05B 17/00 504/101 |

FOREIGN PATENT DOCUMENTS

| | | |
|---|---|---|
| CN | CN102745770 A | 10/2012 |
| WO | WO0032048 A1 | 6/2000 |
| WO | WO0038513 A1 | 7/2000 |
| WO | WO2009007964 A2 | 1/2009 |
| WO | WO2012038480 A2 | 3/2012 |
| WO | WO2014082138 A1 | 6/2014 |
| WO | WO2014158912 A1 | 10/2014 |

OTHER PUBLICATIONS

Badra et al., The relationship between phenolic content and Tylenchulus semipenetrans populations in nitrogen-amended citrus plants, Revue Nematol (1979), 2(2):161-164.
Chitwood, Phytochemical Based Strategies for Nematode Control, Annu Rev Phytopathol (2002), 40:221-249.
Mahajan et al., Nematicidal activity of some phenolic compounds against Meloidogyne incognita, Rev Nematol (1985), 8:161-164.
Nitao et al., In vitro assays of Meloidogyne incognita and Heterodera glycines for detection of nematode-antagonistic fungal compounds, J Nematol (1999), 31(2):172-183.
Ohri et al., Effect of phenolic compounds on nematodes—A review, J Appl Nat Sci (2010), 2(2):344-350.
Roy et al., Plant Nutrition for Food Security—A guide for integrated nutrient management, Food and Agriculture Organization of the United Nations—FAO Fertilizer and Plant Nutrition Bulletin 16, Rome, Italy, 2006.

(Continued)

*Primary Examiner* — Ralph Gitomer
(74) *Attorney, Agent, or Firm* — Khin K. Chin; Bret E. Field; Bozicevic, Field & Francis LLP

(57) ABSTRACT

Aspects of the invention include compositions for controlling plant parasitic nematodes. Compositions according to certain embodiments include a carbon skeleton energy compound, a chelating agent, macronutrients, micronutrients, an ionophore, exotic micronutrients and a plant parasitic nematode antagonist. Methods for using the compositions of the invention to control plant parasitic nematodes and kits having one or more compositions for controlling plant parasitic nematodes are also described.

9 Claims, No Drawings

(56) References Cited

OTHER PUBLICATIONS

Schafer et al., A calcium-channel homologue required for adaptation to dopamine and serotonin in Caenorhabditis elegans, Nature (1995), 375(6526):73-78.
Wu et al., Allelochemicals in wheat (*Triticum aestivum L.*): Cultivar differences in the exudation of phenolic acids, J Agric Food Chem (2001), 49(8):3742-3745.

* cited by examiner

COMPOSITIONS FOR CONTROLLING PLANT PARASITIC NEMATODES

CROSS-REFERENCE TO RELATED APPLICATIONS

Pursuant to 35 U.S.C. §119 (e), this application claims priority to the filing date of the U.S. Provisional Patent Application Ser. No. 61/899,023 filed Nov. 1, 2013; the disclosure of which application is herein incorporated by reference.

INTRODUCTION

Plant-parasitic nematodes are nearly microscopic, worm-shaped animals generally invisible to the naked eye when in the soil. They can cause significant plant damage ranging from negligible injury to total destruction of plant material. The majority of these parasites feed on underground parts of plants, including roots, bulbs, and tubers resulting in below ground, "hidden" feeding activity, which cause damage to plants that cannot always be identified until the plant has suffered from extensive damage.

Controlling the population of plant parasitic nematodes is not a simple event. Many fumigants used to eliminate plant parasitic nematodes from the soil of farms and crop plots were banned in the United States during the mid-1960s because of their severe toxicity and there are some nematode problems for which there currently is no legal, effective nematicide. Chemical management can also sometimes reduce problematic nematode populations for a limited period of time with nematode activity re-emerging once the nematocide is no longer present.

SUMMARY

Aspects of the invention include compositions for controlling plant parasitic nematodes. Compositions according to certain embodiments include a carbon skeleton energy compound, a chelating agent, macronutrients, micronutrients, an ionophore, exotic micronutrients and a plant parasitic nematode antagonist. Methods for using the compositions of the invention to control plant parasitic nematodes and kits having one or more compositions for controlling plant parasitic nematodes are also described.

In embodiments of the invention, compositions for controlling plant parasitic nematodes are provided and include a carbon skeleton energy compound, a chelating agent, macronutrients, micronutrients, an ionophore, exotic micronutrients and a plant parasitic nematode antagonist. In some instances, the plant parasitic nematode antagonist is a microbial plant parasitic nematode antagonist, such as a bacterial plant parasitic nematode antagonist. In these embodiments, the bacterial antagonist may be a nematophagous bacteria. In other embodiments, the microbial antagonist may be a parasitic bacteria, cry protein-forming bacteria, Rhizobacteria, opportunistic parasitic bacteria, endophytic bacteria, parasporal crystal-forming bacteria or symbiotic bacteria. In other instances, the plant parasitic nematode antagonist is a phenolic compound, such as pyrocatechol, propenylphenol, chavicol, chavibetol, chavibetol acetate, allylpyrocatechol, allylpyrocatechol acetate, methyl 4-hydroxybenzoate, methyl 4'-hydroxycinnamate, salicylic acid, hydroquinone, phloroglucinol, pryogallol, orcinol, demethyleugenol, 4-vinylphenol, vanillic acid, caffeic acid, syringic acid, o-coumaric acid, 3-undecylphenol, 3-(8Z-tridecenyl)-phenol, 3-n-butyl-4,5-dihydrophthalide, diphenylheptanoids, lignans, (−)-nortrachelogenin, (+)-pinoresinol, methyl ferulate, pinosylvin monomethyl ether, bursehernin and matairesinol. In yet other instances, the plant parasitic nematode antagonist is a sulfonated compound, such as an alkanesulfonate or arylsulfonate plant parasitic nematode compound.

Aspects of the invention also include methods for using the subject compositions to control plant parasitic nematodes in the soil of one or more target plants. In some embodiments, methods include administering the composition to the top soil of the target plants by a hand-held applicator or by ground-level mechanical machinery. In other embodiments, methods include administering the composition to the top soil of the target plants by aircraft (e.g., helicopter, airplane). In yet other embodiments, methods include mixing the subject compositions with soil and applying the composition-soil mixture to the soil of the target plants. In certain embodiments, methods include applying the composition to the foliage of the target plants by a hand-held applicator, ground level mechanical machinery or by aircraft.

Aspects of the invention also include methods for evaluating the effect of the composition on the plant parasitic nematode population in the soil. In some embodiments, methods include administering the subject compositions to the soil or foliage of the target plants and evaluating the health of plant parasitic nematodes exposed to the subject compositions in the soil. In certain instances, evaluating the health of plant parasitic nematodes exposed to the subject compositions includes evaluating the size of fat globules in the intestinal tract of the nematodes or measuring the size of the gonads of the nematodes. In certain embodiments, methods also include evaluating the sap composition of the one or more plants contacted with the subject compositions. In other embodiments, methods also include evaluating the soil composition, such as the microbial activity of the soil contacted with the subject compositions.

Applications for the subject composition include reducing the overall negative effects of plant parasitic nematodes on the subject plants, improving the overall nutritional health and sap composition of the subject plants, increasing the resistance of the subject plants to plant parasitic nematodes, increasing the overall production of crops from the reduced detrimental effects of plant parasitic nematodes, and the like.

DETAILED DESCRIPTION

Aspects of the invention include compositions for controlling plant parasitic nematodes. Compositions according to certain embodiments include a carbon skeleton energy compound, a chelating agent, macronutrients, micronutrients, an ionophore, exotic micronutrients and a plant parasitic nematode antagonist. Methods for using the compositions of the invention to control plant parasitic nematodes and kits having one or more compositions for controlling plant parasitic nematodes are also described.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As reviewed above, the present invention provides compositions for controlling plant parasitic nematode populations. In further describing embodiments of the invention, compositions having a carbon skeleton energy compound, a chelating agent, macronutrients, micronutrients, an ionophore, exotic micronutrients and a plant parasitic nematode antagonist are first reviewed in greater detail. Next, methods for using the subject compositions to control plant parasitic nematode population and methods for evaluating the effect of the subject composition on plant parasitic nematodes and the overall health of the subject plants including the sap composition are described. Kits including one or more of the subject compositions are also described.

Compositions for Controlling Plant Parasitic Nematodes

As summarized above, the subject invention provides compositions for controlling plant parasitic nematodes. The term "controlling plant parasitic nematodes" is used in its conventional sense to refer to reducing the overall negative effect of plant parasitic nematodes on plants such that the plants experience a decreased amount of negative effects by the plant parasitic nematodes as compared to plants not treated with the subject composition. The overall negative effect by plant parasitic nematodes may be reduced, such as by reducing the overall number of plant parasitic nematodes (i.e., nematode population extermination) in the soil or by reducing the severity or extent of negative effects of the plant parasitic nematodes (i.e., nematode population remains unchanged but exhibit fewer detrimental effects).

In some embodiments, a reduction in the overall negative effect of plant parasitic nematodes may be reduced severity or extent of damage to the plants by plant parasitic nematodes. Compositions of the invention may reduce the severity of damage by plant parasitic nematodes, in certain instances, by improving the overall nutritional health of the plants (e.g., increased sap complexity as described in greater detail below). In other instances, compositions of interest reduce severity of damage by compromising the health of plant parasitic nematodes. In yet other instances, compositions of interest reduce the severity of damage by plant parasitic nematodes by improving the overall nutritional health of the target plants and compromising the health of plant parasitic nematodes.

In other embodiments, a reduction in the overall negative effect of plant parasitic nematodes may be a reduction in the proliferation of plant parasitic nematodes in the soil. In certain instances, compositions of interest reduce the overall number of plant parasitic nematodes in the soil. In other instances, compositions of interest reduce the density of plant parasitic nematodes located near the vital parts of the target plants (e.g., central roots).

As described in greater detail below, the subject compositions may control plant parasitic nematodes by reducing the severity or extent of negative effects on the subject plants or by reducing the overall number of plant parasitic nematodes in the soil. In certain embodiments, the control of plant parasitic nematodes may be realized by an enhancement in the overall health of the subject plants, where in some instances the desired enhancement ultimately results in greater production of some desirable parameter, such as for example the amount of harvested crop produced.

For example, in some embodiments enhanced overall health of the subject plants by compositions of interest includes an increased amount of harvested crop by 10% or more, such as 25% or more, such as 50% or more, such as 75% or more and including increasing the amount of harvested crop by 100% or more. For example, the increased amount of harvested crop may range from 10% to 100%, such as from 25% to 75% and including from 30% to 60%. In other instances, compositions of interest may increase harvested crop production by 1.5-fold or greater, such as 2-fold or greater, such as 2.5-fold or greater, such as 3-fold or greater, such as 5-fold or greater and including increasing harvested crop by 10-fold or greater. For example, the increased harvested crop may range from 1.5-fold to 25-fold, such as from 2-fold to 20-fold, such as from 3-fold to 18-fold and including from 5-fold to 15-fold. In certain instances, where the harvested crop are fruits or nuts, compositions and methods for controlling plant parasitic nematodes provided by the invention may increase the amount of crop produced by 250 pounds per acre or more, such as 500 pounds per acre or more, such as 1000 pounds per acre or more, such as 1500 pounds per acre or more and including by 2000 pounds per acre or more. For example the harvested crop may be increased from 250 pounds to 5000 pounds, such as from 500 pounds to 4500 pounds, such as from 750 pounds to 4000 pounds and including from 1000 pounds to 3000 pounds.

In certain embodiments, compositions of the invention increase the complexity of the sap of the target plants. By "increase" the complexity of the sap means that the number of different compounds found in the sap of plants treated with the subject is greater as compared to the number of compounds found in the sap of plants not treated with the subject compositions. The number of different compounds found in the sap of plants treated with the subject compositions may be increased by 10% or more, such as 25% or more, such as 50% or more, such as 75% or more and including increasing the number of sap constituents by 100% or more. For example, the number of sap constituents may be increased from 10% to 100%, such as from 15% to 95%, such as from 25% to 75% and including from 30% to 70%. In other instances, compositions of interest may increase number of sap constituents by 1.5-fold or greater, such as 2-fold or greater, such as 2.5-fold or greater, such as 3-fold or greater, such as 5-fold or greater and including increasing the number of sap constituents by 10-fold or greater. For example, the number of sap constituents may be increased from 1.5-fold to 10-fold, such as from 2-fold to 9-fold, such as from 3-fold to 8-fold and including from 4-fold to 7-fold.

In other embodiments, enhanced overall health of the subject plants by controlling plant parasitic nematodes with compositions of interest is realized by an improvement in the quality of harvested crops (e.g., color, taste, duration of shelf life, etc.) as compared to harvested crops not treated with the subject compositions.

In yet other embodiments enhanced overall health of the subject plants by compositions of interest includes increased resistance to detrimental effects of pathogens (bacteria, viruses), pests (e.g., mites, aphids, psyllids, etc.) and chemical toxins (such as herbicides, insecticides, fungicides, miticides and other chemical compounds which exhibit phytotoxicity). By increased resistance to the detrimental effects of pathogens, pests and chemical toxins is meant that the amount required to result in detrimental effects on the subject plants is greater as compared to plants not exposed to the subject compositions. For example, the amount of pathogens, pests or chemical toxins required to cause detrimental effects to plants treated with the subject compositions may be increased by 10% or more, such as 25% or more, such as 50% or more, such as 75% or more and including by 100% or more as compared to plants not treated with the subject compositions. In other instances, the amount of pathogens, pests or chemical toxins required to cause detrimental effects to plants treated with the subject compositions may be increased by 1.5-fold or greater, such as 2-fold or greater, such as 2.5-fold or greater, such as 3-fold or greater, such as 5-fold or greater and including by 10-fold or greater as compared to plants not treated with the subject compositions.

In certain embodiments of the invention, compositions of interest are dry. By "dry" is meant that the subject compositions contain little to no water. Accordingly, in these embodiments compositions of interest are formulations which include 1% w/w water or less, such as 0.5% w/w water or less, such as 0.25% w/w water or less, such as 0.1% w/w water or less, such as 0.05% w/w water or less, such as 0.01% w/w water or less and including 0.001% w/w water or less. As such, compositions of the invention are solid compositions provided in fine grain or powder form. In some embodiments, the composition is in the form of an amorphous powder. In some embodiments, the composition is in the form of crystals. Depending on the type of target plants and whether the composition will be applied to the foliage or soil, the size of particles of the compositions varies ranging from 0.01 µm to 100 µm, such as from 0.1 µm to 75 µm, such as from 1 µm to 50 µm, such as from 2.5 µm to 25 µm and including from 5 µm to 10 µm. In certain embodiments, compositions include particles which all have the same size (i.e., are monodisperse or uniform). In other embodiments, compositions include particles which have varying sizes (i.e., are polydisperse). For example, where the subject composition has uniform particle sizes, each component of the composition may be passed through a mesh screen (e.g., a 2-mesh screen) sufficient to uniformly reduce the granular size of each component. In other embodiments, each component may have distinct particle sizes resulting in a polydisperse powder composition. In certain embodiments, compositions of interest are hygroscopic powders and precautionary measures need be taken to prevent absorption of atmospheric moisture, such as for example by including a desiccant.

In certain embodiments, the subject compositions are aqueous compositions, and accordingly include amount of water. The amount of water present in the composition may vary depending on whether the composition is a concentrated or dilute composition. Compositions of interest may include in certain instances from about 5% to about 25% water, from about 25% to about 50% water, from about 50% to about 75% water and including from about 75% to about 90% water. As such, where compositions of interest are aqueous compositions, the amount of water may be 90% w/w or less, such as 80% w/w or less, such as 70% w/w or less, such as about 60% w/w or less, such as about 50% w/w or less, such as about 40% w/w or less, such as 30% w/w or less and including 20% w/w or less.

As summarized above, compositions of interest are compositions for controlling plant parasitic nematodes and include a carbon skeleton energy compound, a chelating agent, macronutrients, micronutrients, an ionophore, exotic micronutrients and a plant parasitic nematode antagonist. Each of the different components of the compositions is now reviewed in greater detail. The amount of each component may vary in the subject compositions depending on the amount and type of subject plants or method employed. As such, the amounts of each component may be varied as desired, such as by increasing or reducing the amount or ratio of a particular component in the composition prior to application.

Plant Parasitic Nematode Antagonists

In embodiments of the invention, compositions for controlling plant parasitic nematodes include one or more plant parasitic nematode antagonists. The term "plant parasitic nematode antagonist" as used herein refers the group of compounds which are active against nematodes and may include repellents, growth inhibitors, reproductive inhibitors, nematotoxicants. As such, plant parasitic nematode antagonist according to embodiments of the invention may antagonize plant parasitic nematodes by inhibiting reproduction of new plant parasitic nematodes, killing plant parasitic nematodes, inhibiting or retarding the growth of existing plant parasitic nematodes or combinations thereof.

Plant parasitic nematode antagonists according to embodiments of the invention may be naturally occurring or synthetic. For example, plant parasitic nematode antagonists may be a phenolic compound, a sulfonated compound, a microbial antagonist, polythienyls, isothiocyanates, glucosinolates, cyanogenic glycosides, polyacetylenes, alkaloids, lipids, terpenoids, sesquiterpenoids, diterpenoids, quassinoids, steroids, triterpenoids, among other plant parasitic nematode antagonists. Compositions of interest may include 1 or more plant parasitic nematode antagonists, such as 2 or more, such as 3 more, such as 4 more or and including 5 or more plant parasitic nematode antagonists. For example, the subject compositions may include from 1 to 10 plant parasitic nematode antagonists, such as from 2 to 9 plant parasitic nematode antagonists, such as from 3 to 8 plant parasitic nematode antagonists and including from 4 to 7 plant parasitic nematode antagonists. Where more than one plant parasitic nematode antagonist is present in the subject compositions, each may be from the same category of plant parasitic nematode antagonists (e.g., phenolic compound, sulfonated compound) or may be from different categories, as desired. For example, in certain instances, compositions of interest may include a phenolic plant parasitic nematode antagonist and a sulfonated plant parasitic nematode antagonist. In other instances, compositions may include a phenolic plant parasitic nematode antagonist and microbial plant parasitic nematode antagonist. In yet other instances, compositions may include a sulfonated plant parasitic nematode antagonist and microbial plant parasitic nematode antagonist. In yet other instances, compositions may include a phenolic plant parasitic nematode antagonist, a sulfonated plant parasitic nematode antagonist and microbial plant parasitic nematode antagonist.

In some embodiments, the plant parasitic nematode antagonist is a phenolic compound. Phenolic plant parasitic nematode antagonists include, but are not limited to, pyrocatechol, propenylphenol, chavicol, chavibetol, chavibetol acetate, allylpyrocatechol, allylpyrocatechol acetate, methyl 4-hydroxybenzoate, methyl 4'-hydroxycinnamate, salicylic acid, hydroquinone, phloroglucinol, pryogallol, orcinol, demethyleugenol, 4-vinylphenol, vanillic acid, caffeic acid, syringic acid, o-coumaric acid, 3-undecylphenol, 3-(8Z-tridecenyl)-phenol, 3-n-butyl-4,5-dihydrophthalide, diphenylheptanoids, lignans, (−)-nortrachelogenin, (+)-pinoresinol, methyl ferulate, pinosylvin monomethyl ether, bursehernin, tannins, proanthocyanadins, flavone glycosides linaroside and lantanoside, coumestrol, psoralidin and matairesinol, among other phenolic plant parasitic nematode antagonists.

In some embodiments, the plant parasitic nematode antagonist is a sulfonated compound. Sulfonated plant parasitic nematode antagonists include, but are not limited, to 1-napthol-2-sodium sulfonate, alkylbenzene sulfonate, ethylmethane sulfonate, sodium polyanethol sulfonate, perfluoroalkyl sulfonate, 2,3-dihydroxypropane-1-sulfonate, alkyl naphthalene sulfonate, tricaine methane-sulfonate, 2,2'-azinodi(ethylbenzthiazo-6-sulfonate), esters of methanesulfonic acid and halomethanesulfonic acids such as chloromethanesulfonic acid, dihalosulfonates, quinoyl alkanesulfonates nematocidal 2,4-dihalophenyl esters of ethanesulfonic acid ethers and alcohols, 2,4-dichlorophenyl methanesulfonate, 2,4-dibromopheny-1-methanesulfonate, 2,4 dichlorophenyl ethanesulfonate, 2,4 dichlorophenyl-1-propanesulfonate, 2,4 dichlorophenyl-2-propanesulfonate, 2,4 dichlorophenyl-1-butanesulfonate, 2,4 dibromophenyl ethanesulfonate, 2,4-dichlorophenyl-1-pentanesulfonate, 2,4-dibromophenyl-1-hexanesulfonate, 2-chloro-4-fluorophenyl methanesulfonate, 2-fluoro 4-chlorophenyl methanesulfonate, 2,4-difluorophenyl methanesulfonate, 2-bromo-4-iodophenyl methanesulfonate, 2,4-diiodophenyl methanesulfonate, 2-chloro-4-bromophenyl methanesulfonate, 2-bromo-4-chlorophenyl methanesulfonate, 2,4-dichlorophenyl chloromethanesulfonate, 2,4-dichlorophenyl bromomethanesulfonate, 2,4-dibromo-2,4-dichlorophenyl-2-chloroethanesulfonate, 2,4 dichlorophenyl-1-chloroethanesulfonate, 2,4-dichlorophenyl-1,3-dichloro-2-propanesulfonate, 2,4-dichlorophenyl trichloromethane sulfonate, 2,4 dichlorophenyl dichloromethanesulfonate, 2,4 dichlorophenyl-2,2 dichloroethanesulfonate, 2,4 dichlorophenyl-1,2-dichloroethanesulfonate, 2,4-dichlorophenyl-2,3-dichloro-1-propanesulfonate, among other sulfonated plant parasitic nematode antagonists.

In some embodiments, the plant parasitic nematode antagonist is a microbial plant parasitic nematode antagonist. Microbial plant parasitic nematode antagonists include, but are not limited to, nematophagous bacteria, nematodic parasitic bacteria, cry protein-forming bacteria, Rhizobacteria, opportunistic parasitic bacteria, endophytic bacteria, parasporal crystal-forming bacteria or symbiotic bacteria, among other microbial plant parasitic nematode antagonists.

Other examples of plant parasitic nematode antagonists are summarized in Table 1:

TABLE 1

| Category | Example |
| --- | --- |
| Polythienyls, | polythienyl; 5-(3-buten-1-ynyl)-2,2'-bithienyl; α-terthienyl |
| Isothiocyanates and Glucosinolates | allyl isothiocyanate; glucosinolate-derived isothiocyanates; 2-Phenylethyl isothiocyanate |
| Cyanogenic Glycosides | glycoside dhurrin; linamarin |
| Polyacetylenes | 1-en-3,5,7,9,11-pentayne; thiarubrines (e.g., thiarubrine C); 3-cis,11-trans- and 3-trans,11-trans-trideca-1,3,11-triene-5,7,9-triyne; tridec-1-en-3,5,7,9,11-pentayne; 9,10-epoxyheptadec-16-en-4,6-diyn-8-ol; 1-phenylhepta-1,3,5-triyne 2-phenyl-5-(1-propynyl)-thiophene; methyl 2-trans,8-cis-deca-2,8-diene-4,6-diynoate; 2-cis,8-cis-deca-2,8-diene-4,6-diynoate; heptadeca-1,9-diene-4,6-diyne-3,8-diol |
| Alkaloids | physostigmine; chelerythrine; sanguinarine; bocconine; monocrotaline; N-methylcytisine; anagyrine; matrine; sophocarpine; sophoramide; aloperine; |
| Lipids | butyric acid; myristic acid; palmitic acid; oleic acid; 2-undecylenic acid; methyl pelargonate; ethylene glycol pelargonate; di-n-butyl succinate; sn-glycerol-1-eicosa-9,12-dienoate-2-palmitoleate-3-linoleate; triacontanyl tetracosanoate |
| Terpenoids | linalool; eugenol; menthol; cineole; geraniol; carvacrol; thymol; trans-anethole |
| Sesquiterpenoids | hemigossypol; 6-methoxyhemigossypol; gossypol; 6-methoxygossypol; alantolactone; α-humulene |
| Diterpenoids | odoracin; odoratrin |
| Quassinoids, Steroids and Triterpenoids | chaparrinone; klaineanone; glaucarubolone; saponins; steroidal glycoalkaloids α-tomatine and α-chaconine; steroidal glycosides asparanin I and asparanin B; triterpenoid glycosides albichinin II and sonunin III; triterpenoid saponin acaciasides A and B; triterpenoid camarinic acid |

The amount of the plant parasitic nematode antagonist in compositions of the invention may vary. For example, the amount may range from 0.01 to 100 pounds, such as from 0.025 to 80 pounds, such as from 0.05 to 70 pounds, such as from 0.1 to 50 pounds and including from 0.1 to 40 pounds. As such, the weight percent of the plant parasitic nematode antagonist in the subject compositions may range from 0.01% to 3% w/w, such as 0.05% to 2% w/w, such as 0.1% to 1.5% w/w and including 0.1% to 1% w/w.

Carbon Skeleton Energy Compounds

CSE compounds that find use in the subject compositions are carbon containing substances which provide a readily assimilable source of both carbon and energy. In certain embodiments, the CSE component provides a complex array of various carbon compounds. The carbon skeleton energy component is a $C_2$ to $C_{10}$ containing compound or polymer thereof, e.g., a polymer in which the monomeric units are $C_2$ to $C_{10}$ compounds, such as a polysaccharide, including a $C_4$ to $C_8$ containing compound or polymer.

CSE compounds of interest include: complex organic compositions, such as molasses (e.g. cane, sugar beet, sorghum, etc.), whey, corn steep liquor, grape syrup, maple syrup, corn syrup, etc; sugars, e.g. sucrose, fructose, glucose, lactose, galactose, dextrose, maltose, raffinose, ribose, ribulose, xylulose, xylose, amylose, arabinose, etc.; sugar phosphates, e.g. fucose-P, galactose-P, glucose-P, lactose-P, maltose-P, mannose-P, ribose-P, ribulose-P, xylose-P, xylulose-P, etc.; sugar alcohols, e.g. adonitol, sorbitol, mannitol, maltitol, ribitol, galactitol, glucitol, etc.; organic acids, e.g. gluccuronic acid, alpha ketoglutaric acid, galactonic acid, glucaric acid, gluconic acid, pyruvic acid, polygalacturonic acid, citric acid, succinic acid, malic acid, isocitric acid, folic acid, etc.; nucleotides and bases, e.g. adenosine, adenosine-P, uridine, uridine-P, thymine, thymine-P, cytosine, cytosine-P, guanine, guanine-P, etc.; and amino acids, e.g. glycine, alanine, leucine, isoleucine, asparagine, tyrosine, phenylalanine, serine, cysteine, valine, proline, methionine, glutamine, threonine, lysine, aspartic acid, glutamic acid, arginine, and the like.

In embodiments of the invention, the amount of CSE component in the composition ranges from about 5% to 75% w/w, such as 10% to 60% w/w, such as 15% to 50% w/w, such as 20% to 40% w/w and including 25% to 35% w/w.

The CSE component may be a single carbon containing compound or a combination of two or more different carbon containing compounds. For example, in some embodiments compositions include two or more carbon containing compounds or polymers, such as where the subject compositions include three or more carbon containing compounds or polymers, such as 4 or more carbon containing compounds or polymers and including 5 or more carbon containing compounds or polymers. Where the CSE component includes two more carbon containing compounds or polymers, the percent by weight of each carbon containing compound in compositions of interest may vary, ranging from 5% to 75% w/w, such as 10% to 60% w/w, such as 15% to 50% w/w, such as 20% to 40% w/w and including 25% to 35% w/w. In certain embodiments, the CSE component is a single carbon containing compound or polymer. In some instances, the carbon skeleton energy compound is corn syrup. In other instances, the carbon skeleton energy compound is cane molasses.

Macronutrients

As noted above, the compositions include one or more macronutrients. As the macronutrient component is a compound that is used by the subject plants, it is typically water soluble so as to be in a form that may be easily used by a plant. The subject compositions may include one or a plurality of macronutrient components.

Accordingly, the number of macronutrient components present in a composition may range from 1 to 15 or more, e.g., from 1 to 6, e.g., from 2 to 6.

The total amount of macronutrient component present in a given composition (whether one or a plurality of macronutrients) depends on a variety of factors such as the particular plant to which the composition is to be administered, the particular macronutrient component(s) employed, and the like. In many embodiments, the total amount of macronutrient component in the composition may range from about 0.01% to about 25% w/w, e.g., from about 1% to about 20% w/w, e.g., from about 1 to about 15% w/w. Exemplary macronutrient components include, but are not limited to one or more of: N, P, K, Ca, Mg, S, CI, Na, C, H, O. For example, certain embodiments may include one or more of the following exemplary macronutrient components:

R—ammonium nitrate, monoammonium phosphate, ammonium phosphate sulfate, ammonium sulfates, ammonium phosphatenitrate, diammonium phosphate, ammoniated single superphosphate, ammoniated triple superphosphate, nitric phosphates, ammonium chloride, aqua ammonia, ammonia-ammonium nitrate solutions, calcium ammonium nitrate, calcium nitrate, calcium cyanamide, sodium nitrate, urea, urea-formaldehyde, urea-ammonium nitrate solution, nitrate of soda potash, potassium nitrate, amino acids, proteins, nucleic acids P—superphosphate (single, double and/or triple), phosphoric acid, ammonium phosphate, ammonium phosphate sulfate, ammonium phosphate nitrate, diammonium phosphate, ammoniated single superphosphate, ammoniated single superphosphate, ammoniated triple superphosphate, nitric phosphates, potassium pyrophosphates, sodium pyrophosphate, nucleic acid phosphates K—potassium chloride, potassium sulfate, potassium gluconate, sulfate of potash magnesia, potassium carbonate, potassium acetate, potassium citrate, potassium hydroxide, potassium manganate, potassium phosphate, potassium molybdate, potassium thiosulfate, potassium zinc sulfate Ca—calcium ammonium nitrate, calcium nitrate, calcium cyanamide, calcium acetate, calcium acetylsalicylate, calcium borate, calcium borogluconate, calcium carbonate, calcium chloride, calcium citrate, calcium ferrous citrate, calcium gluconate, calcium glycerophosphate, calcium lactate, calcium oxide, calcium pantothenate, calcium proprionate, calcium saccharate, calcium sulfate, calcium tartrate Mg—magnesium oxide, dolomite, magnesium acetate, magnesium bensoate, magnesium bisulfate, magnesium borate, magnesium chloride, magnesium citrate, magnesium gluconate, magnesium nitrate, magnesium phosphate, magnesium salicylate, magnesium sulfate S—ammonium sulfate, ammonium phosphate sulfate, calcium sulfate, potassium sulfate, magnesium sulfate, sulfuric acid, cobalt sulfate, copper sulfate, ferric sulfate, ferrous sulfate, sulfur, cysteine, methionine Where the macronutrient component includes two or more compounds, the percent by weight of each macronutrient compound in compositions of interest may vary, ranging from about 0.01% to about 25% w/w, e.g., from about 1% to about 20% w/w, e.g., from about 1 to about 15% w/w. In certain embodiments, the macronutrient component includes a single macronutrient. In certain instances, the macronutrient is calcium gluconate.

Micronutrients

In certain embodiments, the subject compositions may also include one or more micronutrient components. As the micronutrient components are components that are used by a plant, they are typically water soluble components so as to be in a form that may be easily used by a plant. The subject compositions may include one or a plurality of micronutrient components. Accordingly, the number of micronutrient components present in a composition may range from about 1 to about 60 or more, e.g., from about 3 to about 55, e.g., from about 4 to about 50.

The total amount of micronutrient component present in a given composition, whether a single or a plurality of micronutrients depends on the type of subject plants and may range from about 0.001 ppm to 500 ppm w/w, such as 0.05 to 400 ppm w/w, such as 0.01 ppm to 300 ppm, such as 0.1 ppm to 250 ppm and including 1 ppm to 200 ppm w/w. Micronutrient compounds of interest include, but are not limited to:

Zn—zinc oxide, zinc acetate, zinc benzoate, zinc chloride, zinc citrate, zinc nitrate, zinc salicylate, ziram.

Fe—ferric chloride, ferric citrate, ferric fructose, ferric glycerophosphate, ferric nitrate, ferric oxide (saccharated), ferrous chloride, ferrous citrate ferrous fumarate, ferrous gluconate, ferrous succinate.

Mn—manganese acetate, manganese chloride, manganese nitrate, manganese phosphate.

Cu—cupric acetate, cupric butyrate, cupric chlorate, cupric chloride, cupric citrate, cupric gluconate, cupric glycinate, cupric nitrate, cupric salicylate, cuprous acetate, cuprous chloride.

B—calcium borate, potassium borohydride, borax, boron trioxide, potassium borotartrate, potassium tetraborate, sodium borate, sodium borohydride, sodium tetraborate.

Mo—molybdic acid, calcium molybdate, potassium molybdate, sodium molybdate.

Co—cobaltic acetate, cobaltous acetate, cobaltous chloride, cobaltous oxalate, cobaltous potassium sulfate, cobaltous sulfate.

Where the micronutrient component includes two or more compounds, the percent by weight of each micronutrient compound in compositions of interest may vary, ranging from about 0.001 ppm to 500 ppm w/w, such as 0.05 to 400 ppm w/w, such as 0.01 ppm to 300 ppm, such as 0.1 ppm to 250 ppm and including 1 ppm to 200 ppm w/w.

Vitamins and Cofactor Composition

Compositions of interest also include one or more vitamin and cofactor compositions. The subject composition may include one or a plurality of vitamin and cofactor components. Accordingly, the number of vitamin and cofactor components present in a composition may range from about 1 to about 20 or more, e.g., from about 3 to about 15, e.g., from about 5 to about 12.

The total amount of vitamin and cofactor component present in a given composition, whether one or a plurality of vitamin/cofactor components depends on a variety of factors such as the subject plants, the particular vitamin cofactor component(s) employed, and the like. In many embodiments, the total amount of vitamin/cofactor component in the composition may range from about 0.001 to 10%, such as 0.01 to 5%, including 0.25 to 3.0% w/w. Vitamin and cofactors of interest include, but are not limited to:

Thiamine—thiamine pyrophosphate, thiamine monophosphate, thiamine disulfide, thiamine mononitrate, thiamine phosphoric acid ester chloride, thiamine phosphoric acid ester phosphate salt, thiamine 1,5 salt, thiamine triphosphoric acid ester, thiamine triphosphoric acid salt, yeast, yeast extract.

Riboflavin—riboflavin acetyl phosphate, flavin adenine dinucleotide, flavin adenine mononucleotide, riboflavin phosphate, yeast, yeast extract.

Nicotinic acid—nicotinic acid adenine dinucleotide, nicotinic acid amide, nicotinic acid benzyl ester, nicotinic acid monoethanolamine salt, yeast, yeast extract, nicotinic acid hydrazide, nicotinic acid hydroxamate, nicotinic acid-N-(hydroxymethyl)amide, nicotinic acid methyl ester, nicotinic acid mononucleotide, nicotinic acid nitrile.

Pyridoxine—pyridoxal phosphate, yeast, yeast extract.

Folic acid—yeast, yeast extract, folinic acid.

Biotin—biotin sulfoxide, yeast, yeast extract, biotin 4-amidobenzoic acid, biotin amidocaproate N-hydroxysuccinimide ester, biotin 6-amidoquinoline, biotin hydrazide, biotin methyl ester, d-biotin-N-hydroxysuccinimide ester, biotin-maleimide, d-biotin p-nitrophenyl ester, biotin propranolal, 5-(N-biotinyl)-3 aminoallyl)-uridine 5'-triphosphate, biotinylated uridine 5'-triphosphate, N-e-biotinyl-lysine.

Pantothenic acid—yeast, yeast extract, coenzyme A.

Cyanocobalamin—yeast, yeast extract.

Phosphatidylcholine—soybean oil, eggs, bovine heart, bovine brain, bovine liver, L-a-phosphatidylcholine, B-acetyl-g-O-alkyl, D-a-phosphatidylcholine(PTCn), B-acetyl-g-O-hexadecyl, DL-a-PTCh,B-acetyl-g-O-hexadecyl, L-a-PTCh, B-acetyl-g-O-(octadec-9-cis-e-nyl), L-a-PTCh, B-arachidonoyl, g-stearoyl, L-a-PTCh, diarachidoyl, L-a-PTCh, dibehenoyl(dibutyroyl, dicaproyl, dicapryloyl, didecanoyl, dielaidoyl, 12 diheptadecanoyl, diheptanoyl), DL-a-PTCh dilauroyl, La-PTCh dimyristoyl(dilauroyl, dilinoleoyl, dinonanoyl, dioleoyl, dipentadeconoyl, dipalmitoyl, distearoyl, diundecanoyl, divaleroyl,B-elaidoyl-a-palmitoyl, B-linoleoyl-a-palmitoyl)DL-a-PTCh di-O-hexadecyl(dioleoyl, dipalmitoyl, B-O-methyl-g-O-hexadecyl, B-oleoyl-g-O-hexadecyl, B-palmitoyl-g-O-hexadecyl), D-a-PTCh dipalmitoyl, L-a-PTCh, B-O-methyl-g-O-octadecyl, L-a-PTCh, B-(NBD-aminohexanoyl)-g-palmitoyl, L-a-PTCh, B-oleoyl-g-O-palmitoyl(stearoyl), L-a-PTCh, B-palmitoyl-g-oleoyl, L-a-PTCh, B-palmitoyl-a-(pyren 1-yl)hexanoyl, L-a-PTCh, B(pyren-1-yl)-decanoyl-g-palmitoyl, L-a-PTCh, B-(pyren-1-yl)-hexanoyl-g-palmitoyl, L-a-PTCh, B-stearoyl-g-oleoyl.

Inositol—inositol monophosphate, inositol macinate, myo-inositol, epi-inositol, myo-inositol 2,2'anhydro-2-c-hydroxymethyl(2-c-methylene-my-oinositol oxide), D-myo-inositol 1,4-bisphosphate, DL-myo-inositol 1,2-cyclic monophosphate, myo-inositol dehydrogenase, myo-inositol hexanicotinate, inositol hexaphosphate, myo-inositol hexasulfate, myo-inositol 2-monophosphate, D-myo-inositol 1-monophosphate, DL-myo-inositol 1-monophosphate, D-Myo-inositol triphosphate, scyllo-inositol.

PABA—m-aminobenzoic acid, O-aminobenzoic acid, p-aminobenzoic acid butyl ester, PABA ethyl ester, 3-ABA ethyl ester.

Where the vitamin and cofactor compositions includes two or more compounds, the percent by weight of each vitamin or cofactor compound in compositions of interest may vary, ranging from about 0.001 to 10%, such as 0.01 to 5%, including 0.25 to 3.0% w/w.

Complexing Agents

In certain embodiments, the subject compositions may also include one or more complexing agents. A "complexing agent" is used to in its conventional sense to refer to an agent that aids in the solubilization of components of the composition and may also serve to tie up ions (e.g., iron or other ions) and preventing formation of precipitates upon application. A complexing agent may be an agent that is capable of complexing with a metal ion. As such, powder or fine forms of oxidized coal, oxidized bituminous material, ironite, volcanic rock, shale, fossilized peat, moss, kelp or seaweed find use in the subject compositions to provide a source of one or more complexing agents. Other complexing agents of interest include, but are not limited to: citric acid, lignosulfonates, e.g., Ca—, K—, Na—, and ammonium lignosulfonates, amino acids, propionic acid and nucleic acids. In some instances, the secondary complexing agent may be a chelating agent, such as ethylenediamin tetraacetatic acid (EDTA), diethylene triamine pentacetic acid (DTPA), nitrolotriacetic acid (NTA), ethylenediaminediacetate (EDDA), ethylenediaminedi(o-hydroxyphenylacetic) acid (EDDHA), hydroxyethylethylene-diaminetriacetic acid (HEDTA), cyclohexane diamine tetraacetic acid (CDTA) and the like. Naturally occurring chelating agents may also be employed. By naturally occurring chelating agent is meant that the chelating agent is a chelating agent that occurs in nature, i.e. not an agent that has been first synthesized by human intervention. The naturally occurring chelating agent may be a low molecular weight chelating agent, where by low molecular weight chelating agent is meant that the molecular weight of the chelating agent does not exceed about 200 daltons. In certain embodiments, the molecular weight of the chelating agent is greater than about 100 daltons.

Naturally occurring low molecular weight chelating agents that may be used are microbial produced chelating agents, where by "microbial produced" is meant that the chelating agent is produced by a microbe, where the microbe is generally a bacterium or a fungus. In many embodiments, the chelating agents are citric acid cycle intermediates and derivatives thereof. Specific chelating agents of interest include: malic acid, succinic acid, oxalacetic acid, ketoglutaric acid and citric acid and amino acids derived from citric acid cycle intermediates, such as glycine (75.1 daltons), alanine (89.1 daltons), serine (105.1 daltons), valine (117.2 daltons), threonine (119.1 daltons), cysteine (121.2 daltons), leucine (131.2 daltons), isoleucine (131.2 daltons), aspariginine (132.1 daltons), glutamine (146.2 daltons), methionine (149.2 daltons), etc. Accordingly, embodiments include compositions that may include a source of at least one naturally occurring chelating agent. By source is meant that the compositions may include the chelating agents or an entity or component that produces the chelating agents. In many embodiments, the source of chelating agents is a living or viable microbial source of chelating agents. For example, the microbial source may be a bacterial or fungal culture which produces the requisite chelating agents.

The total amount of complexing agent present in a given composition (whether one or a plurality of complexing agents) depends on a variety of factors such as the particular plant to which the composition is to be administered, the particular complexing agent(s) employed, and the like. In certain embodiments, the total amount of complexing agent in the composition may range from about 0.01 to about 5% w/w, e.g., from about 0.1% to about 4.5% w/w, e.g., from about 1.0% to about 4% w/w.

Exotic Micronutrient Component

Exotic micronutrients of the subject compositions include a set or collection of non-traditional micronutrients, where the non-traditional micronutrients may be ones that provide ionic elements found in low amounts, e.g., low parts per million to parts per billion range, in virgin soils (i.e., soils that have not been used previously for agriculture). For example, non-traditional micronutrients may be micronutrients that promote the electrostatic bonding of amino acid chains. As such, powder or fine forms of oxidized coal, oxidized bituminous material, ironite, volcanic rock, shale, fossilized peat, moss, kelp or seaweed find use in the subject compositions to provide a source of one or more exotic micronutrients.

In some embodiments, compositions of interest may include 5 or more distinct exotic micronutrient ionic elements, such as 10 or more distinct exotic micronutrient ionic elements, such as 20 or more distinct exotic micronutrient ionic elements, such as 30 or more distinct exotic micronutrient ionic elements, such as 40 or more distinct exotic micronutrient ionic elements and including 50 or more distinct exotic micronutrient ionic elements.

Exotic micronutrient ionic elements of interest include, but are not limited to: Aluminum (Al), Antimony (Sb), Barium (Ba), Beryllium (Be), Bismuth (Bi), Boron (B), Bromine (Br), Cadmium (Cd), Cerium (Ce), Cesium (Cs), Chromium (Cr), Cobalt (Co), Dysprosium (Dy), Erbium (Er), Europium (Eu), Fluorine (F), Gadolinium (Gd), Gallium (Ga), Germanium (Ge), Gold (Au), Hafnium(Hf), Holmium (Ho), Indium (In), Lanthanum (La), Lutetium (Lu), Lithium (Li), Mercury (Hg), Molybdenum (Mo), Neodymium (Nd), Nickel (Ni), Niobium (Nb), Platinum (Pt), Praseodymium (Pr), Rhodium (Rh), Ruthenium (Ru), Samarium (Sm), Scandium (Sc), Selenium (Se), Silica (Si), Silver (Ag), Strontium (Sr), Sulfur (S), Tellurium (Te), Terbium (Tb), Thallium (Tl), Thorium (Th), Thulium (Tm), Tin (Sn), Titanium (Ti), Tungsten (W), Vanadium (V), Ytterbium (Yb), Yttrium (Y), and Zirconium (Zr).

It is noted that sulfur is listed as a possible exotic micronutrient and yet also listed as a possible macronutrient above. In embodiments where the one or more sources of extracted humate include sulfur, sulfur will not be additionally included as a macronutrient. It is further noted that boron, molybdenum and cobalt are all listed as possible exotic micronutrients and yet are also listed as a possible micronutrients above.

Exotic micronutrients may be present in the form of salts which provide for the desired ionic elements. Examples of sources salts are summarized in Table 2. The below list of sources of the exotic are merely representative.

TABLE 2

| Exotic Micronutrient Element | Symbol | Source: Nitrates | Source: Chlorides | Source: Sulfides | Source: Oxides | Source: Misc. |
|---|---|---|---|---|---|---|
| Europium | Eu | $Eu(NO_3)_3$ | $EuCl_3$ | $Eu_2(SO_4)_3$ | $Eu(OH)_3$ $Eu_2O_3$ | |
| Fluorine | F | $FNO_3$ | | | $F_2O$ | $C_2H_4FNO$: Fluoroacetamide $C_2H_3FO_2$: Fluoroacetic Acid $ClFO_4$: Perchlorate |

TABLE 2-continued

| Exotic Micronutrient Element | Symbol | Source: Nitrates | Source: Chlorides | Source: Sulfides | Source: Oxides | Source: Misc. |
|---|---|---|---|---|---|---|
| Gadolinium | Gd | $Gd(NO_3)_3$ | $GdCl_3$ | $Gd_2(SO_4)_3$ | $Gd(OH)_3$ $Gd_2O_3$ | |
| Gallium | Ga | $Ga(NO_3)_3$ | $GaCl_3$ | $Ga_2(SO_4)_3$ | $Ga(OH)_3$ $Ga_2O_3$ | |
| Germanium | Ge | | $Cl_2Ge$ $Cl_4Ge$ | | $GeO_2$ | $F_4Ge$: Tetrafluoride |
| Gold | Au | | $AuCl$ | $Au_2S$ | $Au_2O$ | CAuN: Monocyanide AuI: Monoiodide |
| Hafnium | Hf | | $HfCl_4$ | $Hf(SO_4)$ | $HfO_2$ | |
| Holmium | Ho | | $HoCl_3$ | | $Ho_2O_3$ | $HoB_3$: Bromide $HoI_3$: Iodide |
| Indium | In | | $Cl_3In$ | $In_2O_{12}S_3$ | $In_2O_3$ | InP: Phosphide AsIn: Arsenide |
| Lanthanum | La | $La(NO_3)_3$ | $LaCl_3$ | $La_2(SO_4)_3$ | $La(OH)_3$ $La_2O_3$ | |
| Lithium | Li | $LiNO_3$ | $ClLi$ | $Li_2O_4S$ | $HLiO$ $Li_2O$ | |
| Lutetium | Lu | | $LuCl_3$ | $Lu_2(SO_4)_3$ | $Lu_2O_3$ | |
| Neodymium | Nd | $Nd(NO_3)_3$ | $NdCl_3$ | $Nd_2(SO_4)_3$ | $Nd(OH)_3$ $Nd_2O_3$ | |
| Nickel | Ni | $N_2NiO_6$ | $Cl_2Ni$ | $NiO_4S$ | $H_2NiO_2$ $Ni_2O_3$ | |
| Niobium | Nb | | $Cl_5Nb$ | | $Nb_2O_5$ | $F_4Nb$ Pentafluoride $F_7K_2NbO$ Oxypenafluoride |
| Platinum | Pt | na | na | na | na | |
| Praseodymium | Pr | | $PrCl_3$ | $Pr_2(SO_4)_3$ | $Pr(OH)_3$ $PrO_2$ $Pr_2O_3$ | |
| Rhodium | Rh | | $C_4Cl_2O_4Rh_2$ $Cl_3Rh$ | | | |
| Ruthenium | Ru | | $Cl_3Ru$ $Cl_6H_{42}N_{14}O_2Ru$ | | $O_4Ru$ | |
| Samarium | Sm | | $SmCl_2$ $SmCl_3$ | $Sm_2(SO_4)_3$ | $Sm(OH)_3$ $Sm_2O_3$ | |
| Scandium | Sc | $Sc(NO_3)_3$ | $ScCl_3$ | $Sc_2(SO_4)_3$ | $Sc(OH)_3$ $O_3Sc_2$ | |
| Silicon | Si | | $Cl_4Si$ | $S_2Si$: Disulfide | $OSi$ $O_2Si$ | $F_4Si$: Tetrafluoride CSi: Carbide $Br_4Si$: Tetrabromide |
| Silver | Ag | $AgNO_2$ $Ag(NO_3)_3$ | $AgCl$ $AgClO_4$ | $Ag_2S$ $Ag_2O_4S$ | $AgO$ $Ag_2O$ $C_2Ag_2O_4$ | AgI: Iodide AgF: Fluoride |
| Strontium | Sr | $N_2O_6Sr$ | $Cl_2Sr$ $Cl_2O_6Sr$ | $O_4SSr$ | $OSr$ $O_2Sr$ $H_2O_2Sr$ | $F_2Sr$: Floride |
| Sulfur | S | | $Cl_2S_2$ $Cl_2O_2S$ | | $O_2S$ $O_3S$ | $H_2O_4S$: Sulfuric Acid SI: Iodide $F_4S$: Tetrafluoride |
| Tellurium | Te | | $Cl_2Te$ $Cl_4Te$ | | $O_2Te$ | $Br_2Te$: Tetrabromide $F_6Te$: Tetrafluoride $H_2O_3Te$: Telluric Acid |
| Terbium | Tb | $Tb(NO_3)_3$ | $TbCl_3 6H_2O$ | | $O_3Tb_2$ $Tb_4O_7$ | |
| Thallium | Tl | $NO_3Tl$ | $Cl_3Tl$ | $STl_2$ $O_4STl_2$ | $HOTl$ $OTl_2$ | $C_2H_3O_2Tl$: Acetate |
| Thorium | Th | $N_4O_{12}Th$ | $Cl_4Th$ | $O_8S_2Th$ | $O_2Th$ | $I_4Th$: Iodide |
| Thulium | Tm | $Tm(NO_3)_3$ | $TmCl_3 \cdot 7H_2O$ | $Tm_2(SO_4)_3 \cdot 8H_2O$ | $Tm(OH)_3$ $O_3Tm_2$ | $TM_2(C_2O_4)_3 \cdot 6H_2O$: OOxalate hexahydrate |
| Tin | Sn | | | | $SnO$ | $Sn_4P_3$: Phosphides |
| Titanium | Ti | | $C_{10}H_{10}Cl_2Ti$ $Cl_2Ti$ $Cl_3Ti$ $Cl_4Ti$ | $O_5STi$ $O_{12}S_3Ti_2$ | $O_2Ti$ | $F_4Ti$: Tetrafluoride $H_2Ti$: Hydride |
| Tungsten | W | | | | $O_3W$ | $F_6W$: Hexafluoride $H_2O_4W$: Tungstic Acid |

TABLE 2-continued

| Exotic Micronutrient Element | Symbol | Source: Nitrates | Source: Chlorides | Source: Sulfides | Source: Oxides | Source: Misc. |
|---|---|---|---|---|---|---|
| Vanadium | V | | $Cl_2OV$<br>$Cl_3OV$ | $O_5SV$<br>$S_3V_2$<br>$O_{12}S_3V_2$ | $O_3V_2$<br>$O_5V_2$ | $F_3V$: Trifluoride<br>$F_4V$: Tetrafluoride<br>$F_5V$: Pentafluoride |
| Ytterbium | Yb | $Yb(NO_3)_3$ | $YbCl_3$ | $Yb_2(SO_4)_3$ | $O_3Yb_2$ | |
| Yttrium | Y | $Y(NO_3)_3$ | $YCl_3$ | $Y_2(SO_4)_3$ | $O_3Y_2$<br>$Y(OH)_3$ | |
| Zirconium | Zr | $N_4O_{12}Zr$ | $Cl_4Zr$<br>$Cl_2OZr$ | $O_8S_2Zr$ | $O_2Zr$<br>$H_4O_4Zr$ | $ZrF_4$: Tetrafluoride<br>$ZrH_2$: Hydride<br>$I_4Zr$: Iodide |

The overall amount of exotic micronutrient present may vary where in certain embodiments, the amount ranges from 0.001 ppb to 100 ppb w/w, such as 0.005 ppb to 75 ppb w/w, such as 0.01 ppb to 50 ppb w/w, such as 0.05 ppb to 25 ppb w/w and including 0.01 ppb to 10 ppb w/w.

The amounts of individual exotic micronutrients may be chosen to provide for concentrations of elements as desired, where the desired concentrations of elements may vary, depending on the particular nature of the exotic micronutrient. For example, one class of exotic micronutrients may be viewed as "severe" micronutrients, and includes Hg (Mercury), Cd (Cadmium), Cs (Cesium). The amounts of these micronutrients may be chosen to provide a concentration in the concentrated product ranging from 1 to 10 ppb, such as 7.5 ppb. Another class of exotic micronutrients may be viewed as "intermediate" micronutrients, and includes Se (Selenium), Al (Aluminum), Ba (Barium), Be (Beryllium), B (Boron), Cr (Chromium), Dy (Dysprosium), Ga (Gallium), La (Lanthanum), Ni (Nickel), Ru (Ruthenium), Sr (Strontium), Te (Tellurium), Sn (Tin), V (Vanadium). The amounts of these micronutrients may be chosen to provide a concentration in the concentrated product ranging from 10 to 25 ppb, such as 15 ppb. Another class of exotic micronutrients may be viewed as "Standard I" micronutrients, and includes Mo (Molybdenum), Sb (Antimony), Ce (Cerium), Co (Cobalt), Er (Erbium), Gd (Gadolinium), Ge (Germanium), Hf (Hafnium), Lu (Lutetium), Li (Lithium), Rh (Rhodium), Sm (Samarium), Ti (Titanium), W (Tungsten), Yb (Ytterbium), Zr (Zirconium). The amounts of these micronutrients may be chosen to provide a concentration in the concentrated product ranging from 20 to 40 ppb, such as 35 ppb. Another class of exotic micronutrients may be viewed as "Standard II" micronutrients, and includes Bi (Bismuth), Eu (Europium), Ho (Holmium), Nd (Neodymium), Pt (Platinum), Ag (Silver), Tl (Thallium), Th (Thorium). The amounts of these micronutrients may be chosen to provide a concentration in the concentrated product ranging from 95 to 150 ppb, such as 90 ppb. Another class of exotic micronutrients may be viewed as "Standard III" micronutrients, and includes Br (Bromine), F (Fluorine), Au (Gold), In (Indium), Pr (Praseodymium), Tb (Terbium), Tm (Thulium). The amounts of these micronutrients may be chosen to provide a concentration in the concentrated product ranging from 400 to 1,000 ppb, such as 850 ppb. Another class of exotic micronutrients may be viewed as "Standard IV" micronutrients, and includes Nb (Niobium), Sc (Scandium), Si (Silicon), S (Sulfur), Y (Yttrium). The amounts of these micronutrients may be chosen to provide a concentration in the concentrated product ranging from 2,000 to 3,700 ppb, such as 3,200 ppb.

An embodiment of the an exotic micronutrient component of interest is one that provides ionic species of the following elements in the amounts provided below: (1) Hg (Mercury), Cd (Cadmium), and Cs (Cesium) ranging from 1 to 10 ppb, such as 7.5 ppb; (2) Se (Selenium), Al (Aluminum), Ba (Barium), Be (Beryllium), B (Boron), Cr (Chromium), Dy (Dysprosium), Ga (Gallium), La (Lanthanum), Ni (Nickel), Ru (Ruthenium), Sr (Strontium), Te (Tellurium), Sn (Tin), V (Vanadium) ranging from 10 to 25 ppb, such as 15 ppb; (3) Mo (Molybdenum), Sb (Antimony), Ce (Cerium), Co (Cobalt), Er (Erbium), Gd (Gadolinium), Ge (Germanium), Hf (Hafnium), Lu (Lutetium), Li (Lithium), Rh (Rhodium), Sm (Samarium), Ti (Titanium), W (Tungsten), Yb (Ytterbium), Zr (Zirconium) ranging from 20 to 40 ppb, such as 35 ppb; (4) Bi (Bismuth), Eu (Europium), Ho (Holmium), Nd (Neodymium), Pt (Platinum), Ag (Silver), Tl (Thallium), Th (Thorium) ranging from 95 to 150 ppb, such as 90 ppb; (5) Br (Bromine), F (Fluorine), Au (Gold), In (Indium), Pr (Praseodymium), Tb (Terbium), Tm (Thulium) ranging from 400 to 1,000 ppb, such as 850 ppb; and (6) Nb (Niobium), Sc (Scandium), Si (Silicon), S (Sulfur), Y (Yttrium) ranging from 2,000 to 3,700 ppb, such as 3,200 ppb.

Alternatively, at least some if not all of the micronutrients may be obtained from a naturally occurring source of nutrients, e.g., fulvic acid. In certain embodiments, fulvic acid is itself the exotic micronutrient source. In such embodiments, fulvic acid is used in greater amounts than when it is employed as a complexing agent (e.g., as described in U.S. Pat. No. 6,874,277, herein incorporated by reference), where this greater amount may be 3-fold or more greater, such as 5-fold or more greater. Additional sources of the exotic micronutrient component include, but are not limited to: quarry from Gold (Au) and Copper (Cu) mines; Leonardite; Volcanic Hot Spring Water (Gilroy Hot Springs, Prizmatic Hot Springs—Yellowstone); Ironite Granule (Scottsdale, AZ); and the like.

Ionophore Component

Compositions of interest also include an ionophore. The term "ionophore" is used in its conventional sense to refer to the class of organic compounds that are capable of transporting ions across lipid barriers in a plant cell. Ionophores of interest include, but are not limited to antibiotics, such as Gramicidin A and Valinomycin, and Amino Butyric Acids (ABA), such as D-alpha ABA, DL-alpha ABA, L-alpha ABA, DL-Beta ABA, Gama—ABA (GABA) (e.g., 4-GABA), and the like.

The total amount of ionophore in the subject compositions may range from about 10 ppm to 500 ppm w/w, such as 25 ppm to 450 ppm w/w, such as 50 ppm to 400 ppm w/w, such as 75 ppm to 350 ppm w/w, such as 100 ppm to 300 ppm and including 150 ppm to 250 ppm w/w, for example 200 ppm w/w.

Water

In certain embodiments, the subject compositions are aqueous compositions, and accordingly include amount of water. The amount of water present in the composition may vary depending on whether the composition is a concentrated or dilute composition. Compositions of interest may include in certain instances from about 5% to about 25% water, from about 25% to about 50% water, from about 50% to about 75% water and including from about 75% to about 90% water. As such, where compositions of interest are aqueous compositions, the amount of water may be 90% w/w or less, such as 80% w/w or less, such as 70% w/w or less, such as about 60% w/w or less, such as about 50% w/w or less, such as about 40% w/w or less, such as 30% w/w or less and including 20% w/w or less.

Flowing Agent

In certain embodiments, compositions of interest may include a flowing agent such as for example where the subject compositions are dry compositions (e.g., where the composition includes 1% w/w water or less, such as 0.5% w/w water or less, such as 0.1% w/w water or less, such as 0.05% w/w water or less, such as 0.01% w/w water or less, such as 0.005% w/w water or less and including 0.001% w/w water or less as described above). As such, compositions of the invention are solid compositions provided in fine grain or powder form. Atmospheric moisture, pressure and temperature can each adversely affect powdered and granulated compositions. These conditions can make compositions cake, lump, bridge, clog application equipment and cause packaging and problems with uptake by the subject plants. Accordingly, in some embodiments, the subject dry compositions further include a flowing agent. By "flowing agent" is meant one or more compounds which facilitate the uninterrupted flow of the powdered composition with minimal hang up on the walls of a container. Flowing agents of interest include, but are not limited to corn starch, sifted wheat flour, sifted corn flour, sifted rice flour, commercial anti-caking agents, silica-based anti-caking agents, hygroscopic absorption agents and the like.

Depending on components in the composition, the particle size of the flowing agent may vary, so long as it is sufficient to provide uninterrupted flow and minimal hang up on the walls of the container when applying the composition to the subject plants. For example, the particle size may vary ranging from 0.01 µm to 100 µm, such as from 0.1 µm to 75 µm, such as from 1 µm to 50 µm, such as from 2.5 µm to 25 µm and including from 5 µm to 10 µm.

The total amount of flowing agent in the subject compositions may range from about 10% to 40% w/w, such as 15% to 35% w/w, such as 20% to 30% w/w and including 22.5% to 27.5% w/w.

Organosilincone Surfactant

In certain embodiments, compositions of interest may include one or more organosilicone surfactant. Organosilicone surfactants of interest include, but are not limited to a nonionic organosilicone wetting agent, polyether-polymethylsiloxane copolymer, alkylphenol ethoxylate, polyether-modified polysiloxane, polyalkyleneoxide modified polydimethylsiloxane, polyethoxlated dimethyl siloxanes, silicone polyether co-polymer, heptamethyltrisiloxane, polyalkyleneoxide modified heptamethylsiloxane, polymethylsiloxane copolymer, trisiloxane-8-ethoxylkate, among other organosilicone surfactants.

The total amount of organosilicone surfactant in the subject compositions may range from about 1% to 40% w/w, such as 2% to 35% w/w, such as 3% to 30% w/w and including 5% to 25% w/w.

In certain embodiments, compositions of interest include a carbon skeleton energy compound, a chelating agent, macronutrients, micronutrients, an ionophore, exotic micronutrients and a microbial plant parasitic nematode antagonist. In other embodiments, compositions of interest include a carbon skeleton energy compound, a chelating agent, macronutrients, micronutrients, an ionophore, exotic micronutrients and a phenolic plant parasitic nematode antagonist. In yet other embodiments, compositions of interest include a carbon skeleton energy compound, a chelating agent, macronutrients, micronutrients, an ionophore, exotic micronutrients and a sulfonated plant parasitic nematode antagonist. In yet other embodiments, compositions of interest include a carbon skeleton energy compound, a chelating agent, macronutrients, micronutrients, an ionophore, exotic micronutrients, a phenolic plant parasitic nematode antagonist and a sulfonated plant parasitic nematode antagonist. In yet other embodiments, compositions of interest include a carbon skeleton energy compound, a chelating agent, macronutrients, micronutrients, an ionophore, exotic micronutrients, a phenolic plant parasitic nematode antagonist and a microbial plant parasitic nematode antagonist. In yet other embodiments, compositions of interest include a carbon skeleton energy compound, a chelating agent, macronutrients, micronutrients, an ionophore, exotic micronutrients, a sulfonated plant parasitic nematode antagonist and a microbial plant parasitic nematode antagonist. In yet other embodiments, compositions of interest include a carbon skeleton energy compound, a chelating agent, macronutrients, micronutrients, an ionophore, exotic micronutrients, a phenolic plant parasitic nematode antagonist, a sulfonated plant parasitic nematode antagonist and a microbial plant parasitic nematode antagonist.

Methods for Controlling Plant Parasitic Nematodes

As summarized above, aspects of the invention also include methods for controlling plant parasitic nematodes by applying the subject compositions to the foliage or soil of one or more plants. As described above, the term "controlling plant parasitic nematodes" is used in its conventional sense to refer to reducing the overall negative effect of plant parasitic nematodes on plants such that the plants experience fewer detrimental by the plant parasitic nematodes as compared to plants not treated with the subject compositions.

In some embodiments, a reduction in the overall negative effect of plant parasitic nematodes may be reduced severity or extent of damage by plant parasitic nematodes. Methods of the invention may reduce the severity of damage by plant parasitic nematodes, in certain instances, by improving the overall nutritional health of the plants (e.g., increasing sap complexity). In other instances, the subject methods reduce severity of damage by plant parasitic nematodes by compromising the health of plant parasitic nematodes. In yet other instances, the subject methods reduce the severity of damage by plant parasitic nematodes by improving the overall nutritional health of the plants and compromising the health of plant parasitic nematodes.

In other embodiments, methods of the invention may reduce the overall negative effect of plant parasitic nematodes by reducing the proliferation of plant parasitic nematodes in the soil of subject plants. In certain instances, the subject methods reduce the overall number of plant parasitic nematodes in the soil of target plants. In other instances, the subject methods reduce the density of plant parasitic nematodes located near vital parts of the target plants (e.g., central roots).

In certain embodiments, the control of plant parasitic nematodes may be realized by an enhancement in the overall health of the subject plants, where in some instances the subject methods results in greater production of some desirable parameter, such as for example the amount of harvested crop produced by the subject plants. For example, in some embodiments methods of the invention increase the amount of harvested crop by 10% or more, such as 25% or more, such as 50% or more, such as 75% or more and including increasing the amount of harvested crop by 100% or more. In other instances, the subject methods increase harvested crop production by 1.5-fold or greater, such as 2-fold or greater, such as 2.5-fold or greater, such as 3-fold or greater, such as 5-fold or greater and including increasing harvested crop by 10-fold or greater. For instance, where the harvested crop are fruits or nuts, methods for controlling plant parasitic nematodes provided by the invention may increase the amount of crop produced by 250 pounds per acre or more, such as 500 pounds per acre or more, such as 1000 pounds per acre or more, such as 1500 pounds per acre or more and including by 2000 pounds per acre or more.

Enhanced overall health of the subject plants by controlling plant parasitic nematodes according to the subject methods may, in certain instances, also be realized by an improvement in the quality of harvested crops (e.g., color, taste, duration of shelf life, etc.) as compared to harvested crops not treated with the subject compositions. Enhanced overall health of the subject plants may also include increased resistance to detrimental effects of pathogens (bacteria, viruses), pests (e.g., mites, aphids, psyllids, etc.) and chemical toxins (such as herbicides, insecticides, fungicides, miticides and other chemical compounds which exhibit phytotoxicity). As described above, by increased resistance to the detrimental effects of pathogens, pests and chemical toxins is meant that the amount required to result in detrimental effects on the subject plants is greater as compared to plants not treated by the subject methods. For example, the amount of pathogens, pests or chemical toxins required to cause detrimental effects to plants treated by the subject methods may be increased by 10% or more, such as 25% or more, such as 50% or more, such as 75% or more and including by 100% or more as compared to plants not treated by the subject methods. In other instances, the amount of pathogens, pests or chemical toxins required to cause detrimental effects to plants treated by the subject methods may be increased by 1.5-fold or greater, such as 2-fold or greater, such as 2.5-fold or greater, such as 3-fold or greater, such as 5-fold or greater and including by 10-fold or greater as compared to plants not treated by the subject methods.

In embodiments of the invention, methods include contacting the soil or foliage of one or more plants with the compositions as described above. By contacting is meant that an amount of the composition is placed on the surface of the soil or foliage of the plant(s) to be treated. The subject compositions may also be incorporated into the soil of the target plants, such as by using conventional agricultural equipment, mixers, blenders or compost tumblers. The term "foliage" is used herein to refer to all parts of the plant which are above ground, i.e. above the soil surface, where the term "foliage" may include leaves, stems, flowers, fruit, etc. As such, methods may include applying one or more of the plant parasitic nematode controlling compositions described above to at least one of the leaves, stems, flowers or fruit of subject plants or applying to the surface or incorporating the composition into the soil of the subject plants. The subject plants may be any type of plant which would benefit from controlling plant parasitic nematodes. As such, plants may include fruit-trees, nut-trees, grain crops, legumes, fruit vines, squash vines, vegetables, houseplants, among other types of plants. For example, plants of interest for controlling plant parasitic nematodes may include, but is not limited to crop plants for almonds, kiwifruit, okra, bucket orchid, onion, scallion, cashews, cherimoya, celery, strawberry, American pawpaw, starfruit, brazil nut, beet, mustard, rapeseed, broccoli, cauliflower, cabbage, Brussels sprouts, turnip, beans, chili peppers, bell peppers, papaya, safflower, caraway, chestnut, star apple, watermelon, tangerine, tangelo, coconut, coffee, cola nut, coriander, crownvetch, hazelnut, azarole, cantaloupe, cucumber, squash, pumpkin, zucchini, gourd, guar bean, quince, lemon, lime, orange, carrot, grapefruit, pomelo, hyacinth bean, longan, lychee, persimmon, durian, oil palm, cardamom, loquat, kumquat, buckwheat, feijoa, fig, fennel, soybean, stanhopea, cotton, sunflower, walnut, flax, lupine, macadamia, acerola, apple, mammee apple, mango, sapodilla, alfalfa, rambutan, cactus, prickly pear, sainfoin, passion fruit, avocado, lima bean, kidney bean, string beans, green beans, mung beans, red beans, black beans, pinto beans, allspice, apricot, cherry, plum, peach, nectarine, guava, pomegranate, pear, currant, rose hips, boysenberry, raspberry, blackberry, blueberry, elderberry, cranberry, sesame, eggplant, naranjillo, rowanberry, hog plum, tamarind, cocoa, clover, vanilla, tung tree, vetch, cowpea, black-eyed peas, karate, tomato, grape, dragonfruit, jujube, among other crop plants.

In embodiments of the invention, an amount of compositions of interest as described above is contacted with the soil or foliage of one or more plants. The composition may be contacted with the subject plants by any convenient protocol. In some embodiments, compositions are contacted by aerial application. Aerial application may include, but is not limited to spraying, dusting and otherwise applying the subject compositions by agricultural aircraft, crop-dusting airplanes, gliders, helicopters, ultra-lights, biplanes, remote control airplanes, as well as motorized, mechanically or electrically powered sprayers or dusters supported by an elevated apparatus (e.g., towers, hydraulic lifts, cranes or support columns). In other embodiments, compositions may be contacted with the subject plants on the ground using motorized, mechanically or electrically powered applicators, such as a tractor or other agricultural vehicle equipped with a sprayer, duster or blower or by hand-held sprayers, blowers, dusters and the like. Compositions may alternatively be manually applied (i.e., by hand). In certain embodiments, the composition is applied using a hand-held sprayer or duster with squirrel cage fan (e.g., where compositions of interest are dry compositions).

The amount of the composition employed during any single application may vary depending on the number of plants, size of the plants, geographical area and environmental conditions (e.g., wind conditions, precipitation, etc.). Any amount may be applied so long as the amount is sufficient to control plant parasitic nematodes as desired. In some embodiments, the amount applied per acre may range from about 0.01 to 10 pounds per acre, such as 0.05 to 9 pounds per acre, such as 0.1 to 8 pounds per acre, such as 0.5 to 7 pounds per acre, such as 1 to 6 pounds per acre and including 2 to 5 pounds per acre. Depending on the type of subject plants, environmental conditions and type and amount of plant parasitic nematodes targeted, the subject compositions may be applied periodically (i.e., in predetermined time intervals). As such, the composition may be applied daily, weekly, every two weeks, monthly etc. In certain embodiments, the subject compositions are applied twice during bloom. Alternatively, the subject compositions may be simply applied as needed, where control of plant parasitic nematode populations have been determined to be necessary or desired as by a trained agriculturalist or apiculturist.

Methods may include a single application of the subject compositions or may include multiple application intervals. By "multiple application intervals" is meant more than a single application of the composition, i.e., one or more subsequent application of the composition is performed after the first application. In practicing methods of the invention, protocols may include two or more application intervals, such as three or more application intervals, such as four or more application intervals and including five or more application intervals.

The duration between application intervals may vary depending on the size and number of plants, geographical location, environmental conditions, size, the type of plant parasitic nematodes identified in the soil of the subject plants, the extent of damage to subject plants by existing plant parasitic nematodes, etc. In certain instances, the duration between application intervals may be predetermined and follow at regular intervals. For example, the time between application intervals may be 1 hour or longer, such as 2 hours or longer, such as 5 hours or longer, such as 10 hours or longer, such as 12 hours or longer, such as 24 hours or longer, such as 48 hours or longer, such as 72 hours or longer, such as 96 hours or longer and including 168 hours or longer. Alternatively, the time between application intervals may be on demand, where one or more subsequent applications is performed based on need determined by a trained agriculturalist or apiculturist.

Methods of the invention according to certain embodiment also include determining and assessing the make-up of the soil of the subject plants. Determining the makeup of the soil refers to the analysis of one or more of the properties and/or the components present in the soil. Determining the makeup of the soil may include, but is not limited to, determining the microbial composition, plant pathogen composition, fungal composition, organic matter composition, the metal composition, salt composition, ionic composition, organometallic composition and pH. Any convenient protocol can be employed to determine the makeup of the soil of the subject plants. In some embodiments, prior to analysis, a sample of the soil of the subject plants may be obtained and filtered (e.g., by vacuum filtration) to separate the solid components from any liquid components. Suitable protocols for analyzing soil may include, but are not limited to the use of nuclear magnetic spectroscopy, UV-vis spectroscopy, infrared spectroscopy, high performance liquid chromatography, liquid chromatography-mass spectrometry, inductively coupled plasma emission spectrometry, inductively coupled plasma mass spectrometry, ion chromatography, X-ray diffraction, gas chromatography, gas chromatography-mass spectrometry, flow-injection analysis, scintillation counting, acidimetric titration, and flame emission spectrometry.

In some embodiments, determining and assessing the make-up of the soil includes evaluating the microbial activity of the soil. The microbial activity of the soil may be evaluated using any convenient protocol, such as for example the Formozan test. In certain instances, the Formozan test parameters include:

Sterile soil: 10-50
Little Activity: 60-150
Mild Activity: 200-600
High Activity: 750-1500
Superior Activity: >2000

Where desired, the microbial activity may be increased, such as for example by 2-fold or greater, such as by 3-fold or greater, such as by 4-fold or greater, such as by 5-fold or greater, such as by 10-fold or greater, such as by 50-fold or greater and including increasing microbial activity of the soil by 100-fold or greater. For example, the microbial activity may be increased by from 2-fold to 100-fold, such as from 5-fold to 50-fold and including increasing microbial activity by from 10-fold to 25-fold. Where microbial activity is measured according to the Formozan parameters summarized above, increasing microbial activity may include raising the Formozan test result of the soil to 750 or greater, such as 1000 or greater, such as 1500 or greater, such as 2000 or greater and including 2500 or greater. For example, in certain instances, the microbial activity is raised to about 3000 or less, such as to about 2500 or less, such as to about 2250 or less and including to about 2000 or less.

Determining and assessing the make-up of the soil may be performed at any time as desired. For example, determining and assessing the make-up the soil may be performed at predetermined intervals such as every day, every week, every two weeks, every month, etc. Alternatively, determining and assessing the make-up of the soil may be performed in conjunction with methods for applying the subject compositions as described above. For example, the soil may be sampled between intervals during a multiple application interval. The make-up of the soil may be evaluated 1 hour or later after applying the subject compositions, such as 2 hours or later, such as 3 hours or later, such as 5 hours or later, such as 10 hours or later, such as 12 hours or later, such as 24 hours or later, such as 48 hours or later and including 72 hours or later after applying the subject compositions. In some embodiments, the make-up of the soil is evaluated before treating the soil with the subject compositions. In other embodiments, the make-up of the soil is evaluated after treating the soil with the subject compositions. In yet other embodiments, the make-up of the soil is evaluated both before and after treating the soil with the subject compositions.

In certain embodiments, methods include determining that subject plants is in need of treatment for controlling plant parasitic nematodes. Determining that subject plants is in need of treatment for controlling plant parasitic nematodes may be performed by any convenient protocol, such as determined by a trained professional agriculturalist or apiculturist. In practicing methods of the invention, determining whether subject plants is in need of treatment for controlling plant parasitic nematodes may include assessing the subject plants and evaluating by a human (either alone or with the assistance of a computer, if using a computer-automated program initially set up under human direction) whether the subject plants would benefit from treatment for controlling plant parasitic nematodes.

In some instances, the subject plants may be determined to be in need of treatment for controlling plant parasitic nematodes where the subject plants has shown a 5% or greater decrease in crop production as compared to a suitable control (e.g., previous seasons production), such as a 10% or greater decrease in crop production, such as a 15% or greater decrease in crop production, such as a 20% or greater decrease in crop production and including a 25% or greater decrease in crop production as compared to a suitable control.

In other instances, the subject plants may be determined to be in need of treatment for controlling plant parasitic nematodes where the subject plants has a crop production per area (e.g., pounds of fruits, nuts, vegetables, etc. per acre) which is below a predetermined threshold. For example, the subject plants may be determined to be in need of treatment for controlling plant parasitic nematodes where the crop production per area is 2% or greater below a predetermined threshold, such as 3% or greater below, such as 4% or greater below, such as 5% or greater below and including 10% or greater below a predetermined threshold.

In yet other instances, the subject plants may be determined to be in need of treatment for controlling plant parasitic nematodes by evaluating observable characteristics of target plants in need of plant parasitic nematode antagonism. Observable characteristics of target plants in need of plant parasitic nematode antagonism may include, in some embodiments, uneven foliage shoots, necrotic foliage shoots, defoliage, stunted stem structure, stunted vine structure, chlorosis, stunted leave structure and stunted fruit structure. In certain embodiments, the subject plants may be in need of treatment for controlling plant parasitic nematodes by determining that plant parasitic nematodes have caused physical damage to the subject plants.

Determining whether subject plants is in need of treatment for controlling plant parasitic nematodes may be performed at any time as desired. For example, determining whether subject plants is in need of treatment for controlling plant parasitic nematodes may be performed at predetermined intervals such as every day, every week, every two weeks, every month, etc. Alternatively, determining whether the subject plants is in need of treatment for controlling plant parasitic nematodes may be performed in conjunction with methods for applying the subject compositions as described above. For example, the subject plants may be monitored by human observation or electronic surveillance (e.g., video), between intervals during a multiple application interval and evaluated whether the subject plants is in need of subsequent application intervals. The subject plants may be evaluated for need of treatment for controlling plant parasitic nematodes 1 hour or later after applying the subject compositions, such as 2 hours or later, such as 3 hours or later, such as 5 hours or later, such as 10 hours or later, such as 12 hours or later, such as 24 hours or later, such as 48 hours or later and including 72 hours or later after applying the subject compositions.

Methods of the invention may also include evaluating the overall health of plant parasitic nematodes in the soil of the subject plants. Evaluating the overall health of plant parasitic nematodes in the soil of the subject plants may be performed by a trained professional agriculturalist, plant biologist, pathologist or other nematode expert. In practicing methods of the invention according to certain embodiments, evaluating the health of plant parasitic nematodes in the soil of the subject plants may include taking a representative number of nematodes found in the soil and evaluating the physical structure of the nematodes. In certain instances, evaluating the physical structure of the nematodes include determining the size of fat globules in the intestinal tract of the plant parasitic nematodes. In other instances, evaluating the physical structure includes measuring the size of the gonads of the plant parasitic nematodes. In yet other instances, evaluating the physical structure includes assessing the shape of the gonads of the plant parasitic nematodes. In some embodiments, evaluating the overall health of plant parasitic nematodes includes assessing the microbial activity of the soil.

Evaluating the overall health of plant parasitic nematodes found in the soil of the subject plants may be performed at any time as desired. For example, evaluating the overall health of plant parasitic nematodes may be performed at predetermined intervals such as every day, every week, every two weeks, every month, etc. Alternatively, evaluating the overall health of plant parasitic nematodes may be performed in conjunction with methods for applying the subject compositions as described above. For example, the plant parasitic nematodes from the soil may be sampled from the soil between intervals during a multiple application interval with the overall health of the plant parasitic nematodes being evaluated. The overall health of plant parasitic nematodes found in the soil of the subject plants may be evaluated 1 hour or later after applying the subject compositions, such as 2 hours or later, such as 3 hours or later, such as 5 hours or later, such as 10 hours or later, such as 12 hours or later, such as 24 hours or later, such as 48 hours or later and including 72 hours or later after applying the subject compositions.

In certain embodiments, methods include assessing the effect of the subject compositions on plant parasitic nematodes. In these embodiments, the overall health of the plant parasitic nematodes may be evaluated before and after applying the subject compositions. In certain instances, assessing the effect of the subject compositions on plant parasitic nematodes includes determining that the size of fat globules in the intestinal tract of the plant parasitic nematodes has changed. For example, methods may include determining that the size of fat globules in the intestinal tract is below a predetermined threshold. In these instances, methods may include determining that the size of fat globules in the intestinal tract of the plant parasitic nematodes is reduced by 50% or greater, such as 60% or greater, such as 70% or greater, such as 80% or greater and including determining that the size of fat globules in the intestinal tract of the plant parasitic nematodes is reduced by 90% or greater. In certain instances, methods include determining that the intestinal tract of the plant parasitic nematodes contains no fat globules.

In other embodiments, assessing the effect of the subject compositions on plant parasitic nematodes includes determining that the size and shape of the gonads of plant parasitic nematodes has changed. For example, methods may include determining that the gonads of the plant parasitic nematodes are malformed.

In other instances, methods include determining that the size of the gonads of the plant parasitic nematode is reduced by 50% or greater, such as 60% or greater, such as 70% or greater, such as 80% or greater and including determining that the size of the gonads of the plant parasitic nematode is reduced by 90% or greater.

Methods of the invention according to certain embodiment also include determining and assessing the make-up of the sap of the subject plants. Determining the makeup of the sap refers to the analysis of one or more of the properties and/or the components present in the sap of the subject plants. Determining the makeup of the sap of the subject plants may include, but is not limited to, determining the organic composition, the metal composition, salt composition, ionic composition, organometallic composition, pH, physical properties (e.g., boiling point), electrochemical properties, spectroscopic properties, acid-base properties, polydispersities and isotopic composition of the sap. Any convenient protocol can be employed to determine the makeup of the sap of the subject plants. In some embodiments, prior to analysis, a sample of the sap of the subject plants may be obtained and filtered (e.g., by vacuum filtration) to separate the solid components from the liquid components. Methods for analyzing sap of the subject plants may include, but are not limited to the use of nuclear magnetic spectroscopy, UV-vis spectroscopy, infrared spectroscopy, high performance liquid chromatography, liquid chromatography-mass spectrometry, inductively coupled plasma emission spectrometry, inductively coupled plasma mass spectrometry, ion chromatography, X-ray diffraction, gas chromatography, gas chromatography-mass spectrometry, flow-injection analysis, scintillation counting, acidimetric titration, and flame emission spectrometry.

In certain embodiments, methods include determining that the complexity of the sap of the plants has increased as a result of treatment with the subject compositions. By increased complexity is meant that the number of different compounds (e.g., organic, salt, organometallic, etc.) is greater as compared to the sap of a plant not treated with the subject composition. In certain instances, the sap may be analyzed prior to treating the subject plants with compositions of interest and after a predetermined time (e.g., 1 month, 3 months, 6 months, 1 year, 2 years, etc.) performing analysis of the sap composition to determine that the complexity of the sap has increased as a result of treatment with compositions of the invention. The number of compounds found in the sap of the plants treated with the subject compositions may be increased by 10% or more, such as 25% or more, such as 50% or more, such as 75% or more and including increasing the number of compounds found in the sap of the plants treated with the subject compositions by 100% or more. For example, the number of compounds found in the sap of the plants treated with the subject compositions may be increased from 10% to 100%, such as from 15% to 95%, such as from 25% to 75% and including from 30% to 70%. In other instances, compositions of interest may increase number of sap constituents by 1.5-fold or greater, such as 2-fold or greater, such as 2.5-fold or greater, such as 3-fold or greater, such as 5-fold or greater and including increasing the number of sap constituents by 10-fold or greater. For example, the number of compounds found in the sap of plants treated with the subject compositions may be increased from 1.5-fold to 10-fold, such as from 2-fold to 9-fold, such as from 3-fold to 8-fold and including from 4-fold to 7-fold.

Determining and assessing the make-up of the sap may be performed at any time as desired. For example, determining and assessing the make-up the sap may be performed at predetermined intervals such as every day, every week, every two weeks, every month, etc. Alternatively, determining and assessing the make-up of the sap of may be performed in conjunction with methods for applying the subject compositions as described above. For example, the sap may be sampled between intervals during a multiple application interval. The make-up of the sap may be evaluated 1 hour or later after applying the subject compositions, such as 2 hours or later, such as 3 hours or later, such as 5 hours or later, such as 10 hours or later, such as 12 hours or later, such as 24 hours or later, such as 48 hours or later and including 72 hours or later after applying the subject compositions.

Kits

Also provided are kits, where kits at least include one or more, e.g., a plurality of the subject compositions, as described above. In certain embodiments, the subject compositions in the kits may be provided in a package. For example, the compositions of the kits may be presented in individual pouches, bottles, or analogous containers, to preserve the compositions until use. For example, one form of suitable packaging is an air-tight container, air-tight bag, re-sealable water-tight/air-tight container, water-impermeable plastics material (e.g., polyvinylchloride), etc.

In certain embodiments, kits may include a separate amount of each component of the subject compositions (e.g., carbon skeleton compound, vitamin mix, micronutrients, plant parasitic nematode antagonist, etc.) where the user can mix each component separately in proportions desired, prior to application. In these embodiments, kits may further include one or more containers for mixing the subject compositions as well as a measuring device for portioning out each component, as desired.

As described above, compositions of interest may be dry compositions. In these embodiments, the subject compositions contain little to no water. Accordingly, kits provided herein may further include a dessicant compound which absorbs atmospheric moisture during storage of the subject compositions. In embodiments, the dessicant may be any convenient hygroscopic compound which induces or sustains the moisture content of the subject compositions during storage such that the water content of the subject compositions remains 1% w/w water or less, such as 0.5% w/w water or less, such as 0.25% w/w water or less, such as 0.1% w/w water or less, such as 0.05% w/w water or less, such as 0.01% w/w water or less and including 0.001% w/w water or less. The dessicant may be contained in a separate package so that it does not contaminate the subject compositions, for example in a mesh bag, opened container, or air/water permeable polymeric or non-polymeric package. Dessicants of interest may include, but are not limited to silica gel, propylene glycol, hexylene glycol, butylene glycol, glycerol triacetate, vinyl alcohol, neoagarobiose, glycerol, sorbitol, xylitol, maltitol, polydextrose, quillaia, lactic acid, urea, glycerin, aloe vera gel, activated alumina, aerogel, benzophenone, bentonite clay, calcium chloride, calcium sulfate, colbalt(II) chloride, copper(II) sulfate, lithium chloride, lithium bromide, magnesium sulfate, magnesium perchlorate, molecular sieves, potassium carbonate, sodium, sodium chlorate, sodium chloride, sodium hydroxide, sodium sulfate, sucrose and phosphorus pentoxide, among other dessicants.

Alternatively, compositions of interest may be aqueous compositions. Accordingly, kits provided herein may further include one or more aliquots of water for mixing into the composition.

Kits may further include components for practicing the subject methods, such as devices for applying the compositions to target plants (e.g., nozzle heads for sprayers or applicators), cartridges having a loaded predetermined amount of the subject compositions, measuring cups or devices for portioning desired amounts for application.

In addition, kits may also include instructions for how to use the subject compositions, where the instructions may include information about to how to apply the compositions to the soil or foliage of subject plants (e.g., almond orchards), application interval schedules, and record keeping devices for executing an application interval regimen. The instructions are recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the protocol for obtaining the instructions may be recorded on a suitable substrate.

Utility

The compositions of the subject invention find use in applications where controlling plant parasitic nematodes is needed or desired. Applications for the subject composition include reducing the overall negative effects of plant parasitic nematodes on the subject plants, improving the overall nutritional health and sap composition of the subject plants, increasing the resistance of the subject plants to plant parasitic nematodes, increasing the overall production of crops from the reduced detrimental effects of plant parasitic nematodes, and the like.

In some embodiments, the subject composition reduce the overall negative effects of plant parasitic nematodes on one or more plants, such as by reducing the severity or extent of damage by plant parasitic nematodes or by reducing the proliferation of plant parasitic nematodes in the soil. Compositions of interest also find use in improving the overall health of the subject plants, such as by increasing the complexity of the plant sap, which can further reduce damage caused by plant parasitic nematodes.

The subject methods, i.e., soil or foliar application of the composition, may result in an enhancement of growth of the plant that is treated, as compared to a plant not treated with by the subject methods. By enhancement of growth is meant that over a set period of time, the treated plant attains a higher total mass than the plant not treated with the subject methods. The amount of enhancement will typically be at least about 5%, usually at least about 10% and more usually at least about 25%, where in many embodiments the amount of enhancement may be 50% or greater. In many embodiments, the amount of enhancement will be at least about 100%.

Embodiments of the invention may also result in enhancement of crop yield, e.g., by 5-fold or more, 10-fold or more, 15-fold or more, 20-fold or more, etc, where the amount of enhancement may be 25% or greater, e.g., 50% or greater.

A variety of different plants may be treated according to the subject methods, where such plants include both crop and ornamental plants, as described above.

The following experiments are offered by way of illustration and not by way of limitation.

EXPERIMENTAL

I. Formulation of Composition for Controlling Plant Parasitic Nematodes

Example formulations for compositions to control plant parasitic nematodes according to certain embodiments of the invention are summarized in Tables 3 and 4.

TABLE 3

Example Composition for Application to Soil

| Material | Rate/ 1000 gal | Rate/ 2500 gal | Rate/ 5000 gal | Rate/ 100 ml |
|---|---|---|---|---|
| Water | 96 gal | 240 gal | 480 gal | 9.6 ml |
| Exotic Micronurtient Mix | 20.0 lb | 50 lb | 100 lb | 0.5 g |
| Propionic Acid | 22.0 gal | 32 gal | 64 gal | 0.4 ml |
| Water | 67.0 gal | 100 gal | 200 gal | 2.4 ml |
| Lignosulfonate | 350 gal | 875 gal | 1750 gal | 35.0 ml |
| Corn Steep | 140 gal | 350 gal | 700 gal | 14.0 ml |
| K-Nitrate | 80 lb | 200 lb | 400 lb | 8.0 g |
| Yeast Extract | 25 lb | 63 lb | 126 lb | 2.5 g |
| Cane Molasses | 350 gal | 875 gal | 1750 gal | 35.0 ml |
| 4-GABA | 35 oz | 88 oz | 167 lb | 3.5 oz |
| Fulvic Acid | 35 gal | 88 gal | 167 gal | 3.5 |

TABLE 2

Example Composition for Application to Foliage

| Material | Rate/ 1000 gal | Rate/ 2500 gal | Rate/ 5000 gal | Rate/ 100 ml |
|---|---|---|---|---|
| Corn Syrup | 680 gal | 1700 gal | 3400 gal | 85.0 ml |
| Fulvic Acid | 80 gal | 200 gal | 400 gal | 8.0 ml |
| Exotic Micronutrient Mix | 40 lb | 100 lb | 200 lb | 1.0 ml |
| Vitamin Mix | 10 lb | 25 lb | 50 lb | 1.5 g |
| 4-GABA | 1 kg | 2.5 kg | 5.0 kg | 0.3 g |
| Citric Acid | 50 lb | 150 lb | 300 lb | 1.1 g |
| Integrity Ca | 240 gal | 600 gal | 1200 gal | 24.0 ml |
| Integrity Z422 | 32 gal | 82 gal | 164 gal | 3.2 ml |
| $MgCl_2$ Hexahydrate | 300 lb | 750 lb | 1500 lb | 3.0 g |
| $MgNO_3$ Hexahydrate | 400 lb | 1000 lb | 2000 lb | 5 g |
| Propionic Acid | 12 gal | 30 gal | 60 gal | 1.1 ml |
| $KNO_3$ | 200 lb | 500 lb | 1000 lb | 8.0 g |
| Boric Acid | 40 lb | 100 lb | 200 lb | 0.6 g |

II. Example Protocol for Preparing Composition for Application to Foliage

Steps:
1. Make a premix of Exotic Minerals: Fill the cone bottom tank with 80 gal fulvic acid and 12 gal propionic acid. Place the exotic minerals in a sock and soak until minerals dissolve into the solution
2. Place the exotic minerals premix into the mix tank and dissolve 50 lb citric acid
3. Blend in 680 gal Corn Syrup
4. Blend in and dissolve 10 lb Vitamin Mix
5. Blend in and dissolve 1 kg of 4-GABA
6. With agitation, stir in 240 gal Integrity Ca
7. Follow with 32 gal Integrity Z422
8. Gradually add Mg Chloride and dissolve completely
9. Gradually add Mg Nitrate and dissolve completely
10. Gradually blend in 200 lb $KNO_B$
11. Add 40 lb Solubor and dissolve completely
12. If needed, adjust volume of mix to 1000 gal with water
13. Add sufficient Aqua Shade to achieve green color
14 Filter through a minimum 400-500 mesh bag filtration unit III. Example Protocols for Application of Composition to Soil

| Timing | Materials | Rate/Ac | Comments |
|---|---|---|---|
| Preplant about 7 days before planting | Water CPS Soil Gold Keel Integrity Z422 | 45 gal 40 gal 2 qt 1 gal | Initially, fill the mix tank with full complement of water and begin agitation. Blend in material in the specified order. Inject into a drip system and irrigate onto soil of subject plants to distribute throughout bed |

-continued

| Timing | Materials | Rate/Ac | Comments |
|---|---|---|---|
| | Integrity FG-Micros | 1 gal | volume. Allow at least 7-10 days at 75%-85% FC field capacity before planting. |
| | CPS Soil Prime | 1 gal | |
| | 10% Boron | 5 oz | |
| | Widespread Max | 0.5 oz | |

| Timing | Materials | Rate/Ac | Comments |
|---|---|---|---|
| Planting Transplant | Water | 296 gal | Initially, fill the mix tank with full complement of water and begin agitation. Blend in material in the specified order. Use as transplant water dictates. |
| | CPS Soil Gold | 2 gal | |
| | Keel | 2 qt | |
| | Integrity Z422 | 1 qt | |
| | Integrity FG-Micros | 1 qt | |
| | CPS Soil Prime | 2 qt | |
| | 10% Boron | 1 oz | |
| | Widespread Max | 0.5 oz | |

Ensure that the transplant water is subbing laterally to wet the root ball. The transplant water should get to the root ball and form a junction between the bed water and root ball. In many cases, this root ball remains untouched by irrigation water as the root ball is too coarse in texture to recrive the irrigation water moving laterally across the bed. This mixture is made to accommodate 300 gal of transplant starter mixture per acre.

III. Example In-Season Soil Fertility Program

| Timing | Materials | Rate/Ac | Comments |
|---|---|---|---|
| $1^{st}$ wk postplant | CPS 8-0-6 | 20 gal | Inject for even distribution. |
| | CPS 0-0-7 | 5 gal | Inject after the 8-0-6 has been injected. |
| $2^{nd}$ wk postplant | CPS 4-8-5 | 10 gal | Inject for even distribution. |
| $3^{rd}$ wk postplant | CPS 8-0-6 | 25 gal | Inject for even distribution. |
| | CPS 0-0-7 | 6 gal | Inject after the 8-0-6 has been injected. |
| 4th wk postplant | CPS 4-8-5 | 12 gal | Inject for even distribution. |
| $5^{th}$ wk postplant | CPS 8-0-6 | 25 gal | Inject for even distribution. |
| | CPS 0-0-7 | 10 gal | Inject after the 8-0-6 has been injected. |
| 6th wk postplant | Water | 10 gal | Mix and inject for maintenance treatments for microbial activity |
| | CPS Soil Gold | 2 gal | |
| | Keel | 2 qt | |
| | Integrity Z422 | 1 qt | |
| | Integrity FG-Micros | 1 qt | |
| | 10% Boron | 5 oz | |
| | Widespread Max | 1h oz | |
| 7th wk postplant | CPS 4-8-5 | 12 gal | Inject for even distribution. |
| 8th wk postplant | CPS 8-0-6 | 30 gal | Inject for even distribution. |
| | CPS 0-0-7 | 10 gal | Inject after the 8-0-6 has been injected. |

| Timing | Materials | Rate/Ac | Comments |
|---|---|---|---|
| $9^{th}$ wk postplant | Water | 10 gal | Inject for even distribution. |
| | CPS Soil Gold | 2 gal | This is the Microbial Maintenance Program" (MMP) |
| | Keel | 2 qt | |
| | Integrity Z422 | 1 qt | |
| | Integrity FG-Micros | 1 qt | |
| | 10% Boron | 5 oz | |
| | Widespread Max | 0.5 oz | |
| $10^{th}$ wk postplant | CPS 4-8-5 | 15 gal | Inject for even distribution. |
| $11^{th}$ wk postplant | CPS 8-0-6 | 30 gal | Inject for even distribution. |
| | CPS 0-0-7 | 12 gal | Inject after the 8-0-6 has been |
| $12^{th}$ wk postplant | CPS 8-0-6 | 30 gal | Inject for even distribution. |
| | CPS 0-0-7 | 12 gal | Inject after the 8-0-6 has been |
| $13^{th}$ wk postplant | CPS 4-8-5 | 14 gal | Inject for even distribution. |
| $14^{th}$ wk postplant | Water | 5 gal | Monthly MMP |
| | Keel | 1 gal | |
| | CPS Soil Gold | 2 gal | |
| | CPS Soil Prime | 1 pt | |
| | Integrity Z422 | 1 qt | |
| | Integrity FG-Micros | 1 qt | |
| | 10% Boron | 5 oz | |
| | Widespread Max | 0.5 oz | |
| $15^{th}$ wk postplant | CPS 8-0-6 | 30 gal | Inject for even distribution. |
| | CPS 0-0-7 | 15 gal | Inject after the 8-0-6 has been |
| $16^{th}$ wk postplant | CPS 4-8-5 | 14 gal | Inject for even distribution. |
| $17^{th}$ wk postplant | CPS 8-0-6 | 25 gal | Inject for even distribution |
| $18^{th}$ wk postplant | CPS 0-0-7 | 12 gal | Inject after the 8-0-6 has been |
| | CPS 8-0-6 | 18 gal | Inject for even distribution. |
| $19^{th}$ wk postplant | CPS 0-0-7 | 9 gal | Inject after the 8-0-6 has been |
| | CPS 4-8-5 | 14 gal | Inject for even distribution. |

| Timing | Materials | Rate/Ac | Comments |
|---|---|---|---|
| $20^{th}$ wk postplant | CPS 8-0-6 | 15 gal | Inject for even distribution. |
| | CPS 0-0-7 | 8 gal | Inject after the 8-0-6 has been |
| $21^{st}$ wk postplant | CPS 4-8-5 | 8 gal | Inject for even distribution. |
| $22^{nd}$ wk postplant | Water | 8 gal | Inject for even distribution. |
| | Keel | 1 gal | This is the Microbial |
| | CPS Soil Gold | 1 gal | Maintenance Program (MMP). |
| | Integrity Z422 | 1 qt | |
| | Integrity FG-Micros | 1 qt | |
| | 10% Boron | 5 oz | |
| | Widespread Max | 0.5 oz | |

$23^{rd}$ wk postplant—Harvest of Processing Tomatoes

IV. Example In-Season Foliar Fertility Program

| Timing | Materials | Rate/100 gal | Comments |
|---|---|---|---|
| $1^{st}$ wk postplant ($1^{st}$ Spray) | Foliar Gold FG31 | 3.0 gal | Spray to wet plants preferably in the early morning. |
| | Keel | 1 qt | |
| | Integrity Ca | 3 qt | |
| | Integrity Z422 | 1 qt | |
| | Integrity FG-Micros | 1 pt | |
| | 10% Boron | 5 oz | |
| | K-Nite | 1 lb | |
| | Widespread Max | 3 oz | |
| 5 days after $1^{st}$ spray ($2^{nd}$ Spray) | As in $1^{st}$ spray | | |
| 7 days after $2^{nd}$ spray ($3^{rd}$ Spray) | As in $2^{nd}$ spray | | |
| Beginning of Bloom ($4^{th}$ Spray) | As in $3^{rd}$ spray | | |

-continued

| Timing | Materials | Rate/100 gal Comments |
|---|---|---|
| Mid fruit load (5$^{th}$ Spray) | As in 4$^{th}$ spray | |
| 10 days after 5$^{th}$ spray (6$^{th}$ Spray) | As in 5$^{th}$ spray | |

V. Plant-Parasitic Nematode Control Field Tests
Example A:
Wine Grape Vineyard
Primary PPN species—Ring Nematode [*Criconemella xenoplax*]
Crop type—Alicante Grapevines
Population Density -346 1250 cc soil
Observable Symptoms:
Uneven emergence of shoots and foliage in spring
Stunted vines with uneven, nonuniform vine health
Stunted leaves and chlorosis common
Plants commonly wilt in heat of the day with slow recovery next day
Low yield and low sugar levels
Method:
The vineyard was treated as a contiguous block with 3 vine rows left out as a control. The soil microbial activation consisted of 40 gpa Tilth+1 gallon microbial suspension delivered through the drip system. Maintenance levels of these products were delivered 1×/mo at 1.5 gal Tilth+1 pt microbial suspension. The vines were also initially sprayed with Fusion FG31 @ 1.5 gal/100 gal+Integrity Ca@ 3 qt/100 gal+Z422@ 1qt/100 gal+FG-M@ 1 pt/100 gal+Solubor@ 6 oz+K-Nite@ 1.5 lbs+Silicone Surfactant @ 3 oz all per 100 gal of spray mix. This was initially delivered near bloom and repeated 3× in 5 day intervals. Thereafter the FG31was increased to 3 gal and sprays applied 1×/2 wk at 40 gpa spray volume.
Results:
Control
410 Ring Nematodes/250 cc soil (November evaluation)
Vines with severe stunting and debilitation
Yields approx. 5 tons/acre
Nonuniform health and size of vines exaggeratedly worsened
Brix ~18
Results:
Treated
4 Ring Nematodes/250 cc soil (Ring Nemas found w/minimal fat globules in the intestinal tract; November evaluation)
Cannot see weak areas in the vineyard
Uniform health and size of vines
Yields approx. 17 tons
Example A:
Lemon Grove
Primary PPN Species—Citrus Nematode (*Tylenchulus semipenetrans*)
Crop-Lemon
Population Density—~54,000 J2 Larvae/250 cc soil
Observable Symptoms:
6 year old trees severely defoliated
Much unevenness in the sizes of trees
Terminus of shoots oftentimes necrotic
Roots scarce in the top 1 inch of soil
Root attrition is common, many of which are dark in color from inability to wash soil from gel matrix of female nematode Methods:
The block was treated except for 4 rows left out as a control. The microbial activation was conducted with 40 gallon per acre (gpa) of substrate (Tilth) and 1 gpa of a microbial suspension (Iota). Balanced levels of Nitrogen and Phosphorus were also delivered to compensate for the demands of microbial metabolism. The block was also fertilized with a balanced program utilizing specific, blended fertilizers in ratios that complemented one another for the total, balanced program. Furthermore, the fertility was delivered in increments to avoid taxing the energy of assimilation at any one moment in the seasonal life of the plant.
Results:
Control
The lemon grove left untreated hosted severe decline and uneven health of the trees.
Trees remained severely defoliated and roots could not be found in the top 1' of soil.
The lemon trees manifested even more attrition on the shoot terminus, characteristic of Citrus Nematode damage to the trees.
Results:
Treated
The lemon grove have refoliated after just 6 weeks on the program.
It is difficult to notice the weak areas of the field, as all trees appear uniformly healthy.
Trees have refoliated completely and are a brilliant shiny green.
With just a scaping of the soil with one's boots, you can see the volumous roots that have grown within the top 1' of soil.
Example B
Potatoes
Primary Obstacles—Columbia RKN (*Meloidogyne chitwoodii*) [78/250 cc soil], Lesion Nematode (*Pratylenchus penetrans, P. thomei*) [36/250 cc soil], Stunt Nematode (*Tylenchorhynchus clarus*) [54/250 cc soil], Dagger Nematode (*Xiphinema americanum*) [12/250 cc soil], *Fusarium solani* [356 cfu/gr soil], *Cylindrocarpon obtusisporum* [174 cfu/gr soil], *Rhizoctonia solani* [6 cfu/gr soil]
Methods:
A small pivot (~65 acres) was split in ½ one side received standard fumigation via Telone and Vapam (~30 gal+40 gal). The treated side received a unique microbial activation and superior nutritional progam via both soil application and via foliar treatments. The soil microbial program consisted of 40 gpa Tilth+1 gal Iota. The N and P were adjusted to compensate for the high levels of microbial activation following treatment (UAN-32@ 6 gal+10-34-0@ 2 gal). The remaining soil fertility programs were kept the same utilizing the Grower's Standard Practice. Maintenance levels of microbiology were done with monthly applicatins of 1.5 gpa Tilth+1 pt/ac Iota. The treated potatoes also received 5 foliar sprays during the growing season beginning at hooking and spaced about 10 days apart.
Results:
Control
There were no indications of RKN infestation in the potatoes.
There were no indications of disease in the soil
Potatoes hosted a specific gravity of ~1.075
Potatoes hosted brown core, a physiological problem arising from heat waves The size of spuds from the fumigated block were smaller than the potatoes from the microbially activated soil (e.g. Bakers @ 8oz+→3/vine in control vs 4/vine for treated)

Treated

There were no indications of RKN infestation in the potatoes.

There were no indications of disease in the soil

Potatoes hosted a specific gravity of −1.076

Potatoes hosted brown core, a physiological problem arising from heat waves

The size of spuds from the microbially activated block appeared to be larger than the potatoes from the fumigated soil.

Example D:

Grapevines from Napa Valley

The grapevines are stunted and uneven in their growth and development

Yields have been affected as during heat waves there is a dramatic reduction in turgor pressure and there is much wilting The wilting does not easily subside with the morning cool There is a distinct difference in yields and quality from one year to the next There were 210/250 cc of the American Dagger Nematode [*Xiphinema americanum*] and 160 of X index.

Method:

The vineyard (~20 acres) was split in half with ½ receiving no treatment and the other ½ receiving the microbial activation program. The microbial activation consisted of 35 gpa Tilth+1 gpa Iota. As in other tests, the N and P levels were also adjusted to compensate for microbial metabolism. 6 gpa of UAN-32 and 2 gpa of 10-34-0 were applied to adjust N &: P. The remaining soil programs consisted of—a) maintenance levels of microbial activity 1×/wk at a rate of 2 gpa Tilth+1 pt/ac of Iota. The fertility program consisted of blended fertilizers 8-0-6+0-0-7+4-8-5 incremented throughout the season. Further, from 1 week prior to bloom the vineyard was sprayed with FG31 @ 1.5 gaVlOO g+Integrity Ca@ 3 qt per 100 g+Z422@ 1 qt/100 g+FG-M@ 1 pt/100 g+10% B@ 6 oz+K-Nite@ 1.5 lb/100 g+Silicone Surfactant@ 3 oz/100 g. The 1st 3 sprays were applied at 5 day intervals. Thereafter, the FG31 was increased to 3 g/100 g and sprayed every 10 days throughout the season.

Results:

Control

The grapevines are stunted and uneven in their growth and development

Yields have been affected as during heat waves there is a dramatic reduction in turgor pressure and there is much wilting The wilting does not easily subside with the morning cool There is a distinct difference in yields and quality from one year to the next There were 210/250 cc of the American Dagger Nematode [*Xiphinema americanum*] and 160/250 cc soil of [X. index].

Treated

Grapevines have grown out of their stunted appearance

Yields have increased from an average of 2.5 tons/acre to 8.5 tons/acre

There are no signs of wilting

There is no alternate bearing

What is germane to this test is the absence of disease and RKN infestations of the spuds. There was definitely a background of RKN damages in previous plantings from this field. But the absence of RKN damages indicates that the microbial treatments combined with the special foliar mixes have protected the potatoes in the nonfumigated block from both PPN and soil-borne pathogens.

VI. Field Tests for Disease Control Using Selective Microbial Activation

Example A:

Onion Planting

Primary Obstacles—Pink Root of Onions (*Pyrenochaeta terrestris; Phoma terrestris*); Fusarium Wilt (*Fusarium oxysporum* f.sp. cepae); Fusarium Butt Rot (*F. solani*)

Inoculum Levels—*P. terrestris*@ 84 cfu/gr soil, *F. oxysporum*@ 1,350 cfu/gr soil; F solani@ 650 cfu/gr soil Onions grown in this field are badly diseased with shon storage time, the majority rotting while in storage The field is uneven in the set of seedling+growth and development The plants wilt severely with slow recovery during heat waves The roots are severely degenerated with pink color from *P. terrestris* infections The onion bulbs do not have much integrity of tissues nor any firmness to have sufficient shelf life Methods:

The field was blocked into 20 acres treated with selective microbial activation using 35 gpa Tilth+1 gpa Iota. The requirements for additional N and P were achieved using 6 gpa UAN-32 and 3 gpa 10-34-0. Maintenance levels of soil microbiology were kept with 2 gpa Tilth+1 pt/ac Iota delivered be/month. The seedlings were sprayed with FG31 @ 1.5 &'100 g +Integrity Ca@ 3 qts/100 g+Z422 @ 1 qt/100 g+FG-M@ 1 pt/100 g+10% B@ 6 oz/100 g+K-Nite@ 1.51bs/100 g. After 3 consecutive sprays beginning with 4 true leaves@ 5 day intervals, the rate of FG31 was increased to 3 gaV100 g and sprayed every 10 days throughout the season.

Results:

Control (The Initial Description of Problems has not Changed)

Onions grown in this field are badly diseased with shon storage time, the majority rotting while in storage The field is uneven in the set of seedling+growth and development The plants wilt severely with slow recovery during heat waves The roots are severely degenerated with pink color from *P. terrestris* infections The onion bulbs do not have much integrity of tissues nor any firmness to have sufficient shelf life The levels of plant pathogens remain high: P. terrestris @ 102cfu/gr; *E oxysporum* f. sp. cepae @ 1440cfu/gr; *F. solani* @ 450cfu/gr.

Treated

There was no sign of disease in the field and onions were firm, with high tissue integrity and storage life of −3 months longer without loss of quality The stand was even and the growth and development of plants was uniform and without disease There was no wilting during heat waves There were no signs of pink root The inoculum levels of soil-borne pathogens was dramatically lowered:

F. oxysporum f. sp. cepae @ 12cfu/gr; P. terrestris @ 4 cfu!gr; F. solani@ 20 cfu/gr.

Example B:

Strawberries

Primary Obstacles—Heavy inoculum levels of Venicillium dahliae (@46 cfu/gr soil); Rhizoctonia solani (@14 cfu/gr soil); Phytophthora fragariae (@ 62 cfu/gr soil); Pythium ultimum (@146 cfu/gr soil

- The transplants grow slowly and many are stunted and uneven in size and vigor
- In severe cases, the seedlings wilt and do not recover overnight
- The productivity of the seedlings is poor, giving small sized berries that can only be marketed for processing
- There is an high incidence of sudden vine collapse and when seedlings are examined, the terminus of the roots are dark and necrotic
- In other cases of vine collapse, the seedlings develops a pink to red discoloration of the stele
- Verticillium wilt begins to express itself when vines begin pushing abundant bloom and are setting fruit at the same time
- Strawberry yields are very low for the region (Turlock, Ca); 600 crates of mostly processing berries with very low numbers of restaurant grade berries
- The size of berries were undesirable and their taste is bland and not like a delicious, juicy strawberry should taste Methods 1. The strawberry block of 20 acres was split into two, 10 ac blocks. Block 1 was fumigated with MBr@ 25 gpa with tarping.
2. Strawberry block 2 was treated with a unique soil microbiological activation program:
    a) The soil was ripped and cross-ripped to 4' depth
    b) The uplifted soil was left exposed to drying air and sunlight
    c) 2 weeks following aeration of the soil, the field was disced in both directions to settle the ground and to remove air pockets
    d) The soil was then worked to seedbed quality and fertilized with 40 units of N via Calcium Nitrate+15 units of P via 11-52-0
    e) The field was seeded with 110 lbs/ac Sorghum Sudan and irrigated
    f) When the Sorghum Sudan was -3'-4' tall the grass was mowed and immediately treated with 40 gal Tilth+1 gal Iota.
    g) The grass and activator were incorporated by cross discing then irrigated to wet the $1^{st}$ 2' of soil
    h) The soil was kept near 80%-85% FC for 10 consecutive days without disturbing the soil
    I) Strawberries were transplanted in early August and immediately treated with the following:
        [1] Tilth@ 10 gpa+1 qt Iota+CN-9@ 10 gpa+4 gpa 10-34-0+Phos Acid@ 3 gpa
        [2] Periodic injections of a special blended fertilizer produced by Sunburst PDC, 8-0-6+0-0-7+4-8-5 throughout the season.
        [3] Foliar spray with FG31 @ 3 gal/100 g+Keel@ 1 qt/100 g+Z422@ 1 qt/100 g+FG-M@ 1pt/100 g+10% Boron@ 6 oz/100 g+KN03 @ 1.5 lb/100 g+silicone surfactant@ 3 oz/100 g. The $1^{st}$ 3 sprays were conducted at 5 day intervals and thereafter every 7-10 days during the season
        [4] Monthly maintenance injections of Tilth@ 2 gpa+1 pt Iota Results Control:

- Heavy inoculum levels ofVerticillium dahliae (@54 cfu/gr soil); Rhizoctonia solani (@18 cfu/gr soil); Phytophthora fragariae (@ 52 cfu/gr soil); Pythium ultimum (@126 cfu/gr soil)
- The transplants grow slowly and many are stunted and uneven in size and vigor
- In severe cases, the seedlings wilt and do not recover overnight
- The productivity of the seedlings is poor, giving small sized berries that can only be marketed for processing
- There is an high incidence of sudden vine collapse and when seedlings are examined, the terminus of the roots are dark and necrotic
- In other cases of vine collapse, the seedlings develops a pink to red discoloration of the stele
- Verticillium wilt begins to express itself when vines begin pushing abundant bloom and are setting fruit at the same time
- Strawberry yields are very low for the Oxnard -Santa Maria region; 700 crates of mostly processing berries with very low numbers of restaurant grade berries
- The size of berries were undesirable and their taste is bland and not like a delicious, juicy strawberry should taste Treated:

- Inoculum levels of soil-borne pathogens were dramatically reduced—V. dahlia @ ND; R. solani @ 2 cfu/gr; P. fragariae@ ND; P. ultimum@ 12 cfu/gr
- Transplants grow vigorously, are bushy and uniform in size
- There is no sign of wilting
- There is no incidence of sudden vine collapse
- There are no incidences of red stele nor of Verticillium wilt
- There was considerable improvement in the quality and yield of
- Strawberries from this block; 1,100 crates with better than 70% going for restaurant grade
- Taste, fragrance and shipping quality of the berries reserved for a gift mailing Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An aqueous composition for controlling plant parasitic nematodes, the composition consisting of:
    a carbon skeleton energy compound in an amount of from 20% w/w to 40% w/w;
    a chelating agent in an amount of from 0.1% w/w to 5% w/w;
    a complexing agent in an amount from 0.01% to 5% w/w;
    macronutrients in an amount of from 1% w/w to 15% w/w;
    micronutrients in an amount of from 0.01 ppm to 250 ppm;
    an ionophore;
    exotic micronutrients; and
    one or more plant parasitic nematode antagonists selected from:
        a microbial plant parasitic nematode antagonist in an amount of from 0.01% w/w to 3% w/w;
        a sulfonated plant parasitic nematode antagonist; and
        a phenolic plant parasitic nematode antagonist selected from the group consisting of pyrocatechol, propenylphenol, chavicol, chavibetol, chavibetol acetate, allylpyrocatechol, allylpyrocatechol acetate, methyl 4-hydroxybenzoate, methyl 4'-hydroxycinnamate, salicylic acid, hydroquinone, phloroglucinol, pryogallol, orcinol, demethyleugenol, 4-vinylphenol, vanillic acid, caffeic acid, syringic acid, o-coumaric acid, 3-undecylphenol, 3-(8Z-tridecenyl)-phenol, 3-n-butyl-4,5-dihydrophthalide, diphenylheptanoids, lignans, (−)-nortrachelogenin, (+)-pinoresinol, methyl ferulate, pinosylvin monomethyl ether, bursehernin, tannins, proanthocyanadins, flavone glycosides linaroside and lantanoside, coumestrol, psoralidin and matairesinol,
    wherein the aqueous composition comprises the carbon skeleton energy compound, chelating agent, complexing agent, macronutrients, micronutrients, ionophore, exotic micronutrients and plant parasitic nematode antagonist in an amount sufficient to control plant parasitic nematodes.

2. The composition according to claim 1, wherein the microbial plant parasitic nematode antagonist is selected from the group consisting of nematophagous bacteria, nematodic parasitic bacteria, cry protein-forming bacteria, Rhizobacteria, opportunistic parasitic bacteria, endophytic bacteria, parasporal crystal-forming bacteria and symbiotic bacteria.

3. The composition according to claim 1, wherein the exotic micronutrients are present in an amount ranging from 1 to 15% w/w.

4. The composition according to claim 1, wherein said carbon skeleton energy compound is present in an amount ranging from 25 to 35% w/w.

5. The composition according to claim 1, wherein water is present in the composition in an amount ranging from 50% to 99% w/w.

6. An aqueous composition for controlling plant parasitic nematodes, the composition consisting of:
    a carbon skeleton energy compound in an amount of from 20% w/w to 40% w/w;
    a chelating agent in an amount of from 0.1% w/w to 5% w/w;
    macronutrients in an amount of from 1% w/w to 15% w/w;
    micronutrients in an amount of from 0.01 ppm to 250 ppm;
    an ionophore
    exotic micronutrients;
    a vitamin cofactor composition in an amount of from 0.1% w/w to 5% w/w and
    one or more plant parasitic nematode antagonists in an amount of from 0.01% w/w to 3% w/w selected from a microbial plant parasitic nematode antagonist and a sulfonated plant parasitic nematode antagonist,
    wherein the aqueous composition comprises the carbon skeleton energy compound, chelating agent, macronutrients, micronutrients, ionophore, exotic micronutrients and plant parasitic nematode antagonist in an amount sufficient to control plant parasitic nematodes.

7. A composition for controlling plant parasitic nematodes, the composition consisting of:
    a carbon skeleton energy compound in an amount of from 20% w/w to 40% w/w;
    a chelating agent in an amount of from 0.1% w/w to 5% w/w;
    macronutrients in an amount of from 1% w/w to 15% w/w;
    micronutrients in an amount of from 0.01 ppm to 250 ppm;
    an ionophore;
    exotic micronutrients; and
    a microbial plant parasitic nematode antagonist in an amount of from 0.01% w/w to 3% w/w,
    wherein the carbon skeleton energy compound, chelating agent, macronutrients, micronutrients, ionophore, exotic micronutrients and plant parasitic nematode antagonist are present in an amount sufficient to control plant parasitic nematodes.

8. The composition according to claim 7, wherein the composition is in the form of an amorphous powder.

9. The composition according to claim 7, wherein the composition is in the form of crystals.

* * * * *